(12) United States Patent
Nakayashiki et al.

(10) Patent No.: US 7,611,817 B2
(45) Date of Patent: Nov. 3, 2009

(54) AROMATIC SULFONIUM SALT COMPOUND, PHOTO-ACID GENERATOR COMPRISING THE SAME AND PHOTOPOLYMERIZABLE COMPOSITION CONTAINING THE SAME, RESIN COMPOSITION FOR OPTICAL THREE-DIMENSIONAL SHAPING, AND METHOD OF OPTICALLY FORMING THREE-DIMENSIONAL SHAPE

(75) Inventors: Tetsuyuki Nakayashiki, Tokyo (JP); Hiroyuki Tachikawa, Tokyo (JP)

(73) Assignee: Adeka Corporation, Tokyo (JP)

( * ) Notice: Subject to any disclaimer, the term of this patent is extended or adjusted under 35 U.S.C. 154(b) by 795 days.

(21) Appl. No.: 10/529,015
(22) PCT Filed: Sep. 25, 2003
(86) PCT No.: PCT/JP03/12226

§ 371 (c)(1),
(2), (4) Date: May 13, 2005

(87) PCT Pub. No.: WO2004/029037

PCT Pub. Date: Apr. 8, 2004

(65) Prior Publication Data

US 2006/0055088 A1 Mar. 16, 2006

(30) Foreign Application Priority Data

Sep. 25, 2002 (JP) ............................ 2002-279416
Mar. 26, 2003 (JP) ............................ 2003-085426

(51) Int. Cl.
*G03F 7/00* (2006.01)
*G03F 7/004* (2006.01)

(52) U.S. Cl. .................. 430/270.1; 430/905; 430/913; 430/914; 430/280.1; 430/281.1; 568/18

(58) Field of Classification Search ............. 430/270.1, 430/905, 913, 280.1, 281.1
See application file for complete search history.

(56) References Cited

U.S. PATENT DOCUMENTS 4,250,053 A * 2/1981 Smith .......................... 502/167

5,446,172 A * 8/1995 Crivello et al. ................ 549/62

(Continued)

FOREIGN PATENT DOCUMENTS

JP 57-049613 A 3/1982

(Continued)

OTHER PUBLICATIONS

J. Org. Chem., (1990), 55(13), p. 4222-5.

*Primary Examiner*—Amanda C. Walke
(74) *Attorney, Agent, or Firm*—Birch, Stewart, Kolasch & Birch LLP

(57) ABSTRACT

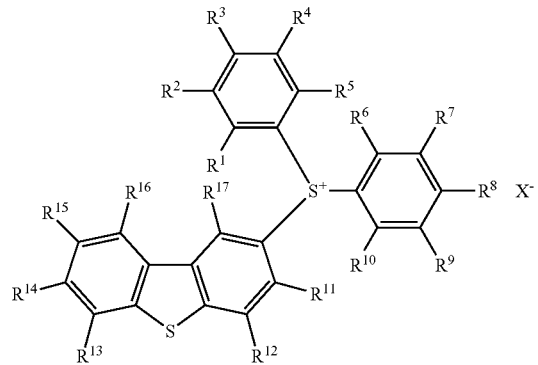

Novel aromatic sulfonium salt compounds of general formula (I), photo-acid generators comprising the same, and photopolymerizable compositions containing the same, capable of providing stereolithographic resin compositions which do not suffer from the hindrance to curing by oxygen, can easily give shaped articles having desired sizes by virtue of the high accuracy thereof in curing, can attain a satisfactory curing depth owing to the high sensitivity thereof for radiant energy and can be employed for wide usage, such as photoresist and ink for foods-packing medium, since the release of benzene is suppressed; and a stereolithographic process, using said stereolithographic resin composition.

10 Claims, 3 Drawing Sheets

U.S. PATENT DOCUMENTS

| | | | |
|---|---|---|---|
| 6,602,969 B2 * | 8/2003 | Ueda et al. | 526/279 |
| 6,773,474 B2 * | 8/2004 | Koehnle et al. | 51/298 |
| 6,880,296 B1 * | 4/2005 | Engelbrecht et al. | 52/25 |
| 6,913,792 B2 * | 7/2005 | Clough et al. | 427/386 |
| 7,026,367 B2 | 4/2006 | Kalgutkar | 522/31 |
| 7,144,927 B1 * | 12/2006 | Engelbrecht et al. | 522/25 |
| 7,230,122 B2 * | 6/2007 | Liu et al. | 549/27 |
| 7,297,724 B2 * | 11/2007 | Kalgutkar | 522/31 |

FOREIGN PATENT DOCUMENTS

| | | | |
|---|---|---|---|
| JP | 58-037004 A | | 3/1983 |
| JP | 06271532 A | * | 9/1994 |
| JP | 06345726 A | * | 12/1994 |
| JP | 08325225 A | * | 12/1996 |
| JP | 10-204083 A | | 8/1998 |
| JP | 10245378 A | * | 9/1998 |
| JP | 11-269212 A | | 10/1999 |
| JP | 2000044535 A | * | 2/2000 |
| JP | 2001-288205 A | | 10/2001 |
| WO | WO-99/28295 A1 | | 6/1999 |

* cited by examiner

AROMATIC SULFONIUM SALT COMPOUND, PHOTO-ACID GENERATOR COMPRISING THE SAME AND PHOTOPOLYMERIZABLE COMPOSITION CONTAINING THE SAME, RESIN COMPOSITION FOR OPTICAL THREE-DIMENSIONAL SHAPING, AND METHOD OF OPTICALLY FORMING THREE-DIMENSIONAL SHAPE

TECHNICAL FIELD

The present invention relates to a novel aromatic sulfonium salt compound, a photo-acid generator comprising the same, a photo-polymerizable composition and a stereolithografic resin composition comprising the said photo-acid generator, and a stereolithografic process. And also, the present invention relates to a photo-polymerizable composition useful as U.V. curable ink for foods-packaging medium.

BACKGROUND ART

Since a photo-polymerizable composition can be used without a solvent, it is preferably used in paint, coating, ink, shaped article as a material in which the load to work environment or terrestrial environment is very small. On the other hand, a photo-polymerizing initiator is essential to cure the photo-polymerizable composition. In the photo-polymerizing initiator, there are a radically polymerizing initiator and a cationically polymerizing initiator.

Although a radically polymerizing initiator has a good performance to show high curing rate, it has defects such as a hindrance to curing by oxygen in air, a shrinkage on curing and the like. Therefore, a cationically polymerizing initiator is more preferably employed.

A photo-acid generator is the substance to release an acid by being exposed to beam, which is useful for cationically polymerizing photo-initiator. Thus, it is used in stereolithographic resin composition and photo-polymerizing composition in paintings, coatings or adhesives. An example of the prior art for such a photo-acid generator, is described in the following Patent document No. 1.

In the Patent document No. 1, an aromatic sulfonium salt compound useful as a photo-acid generator is described, and a cationically polymerizing photo-initiator for epoxy resin, employed the photo-acid generator, and the photo-polymerizable composition employed the initiator are described. Further, a stereolithographic resin composition and a stereolithographic process, employed the composition, are described.

Patent document No. 1:Japanese Patent Application Laid-open No. 2000-186071.(claims, etc.)

A photo-acid generator described in the Patent document No. 1 has a sufficient sensitivity compared with that of the prior art, and provides a photo-polymerizable composition which can be rapidly cure, and a molding having a good precision without the prevention of curing under oxygen. However, the one having the better sensitivity is desirable from the practical view point.

Aryl diazonium salts, which has been used as a cationcally photo-polymerizing initiator in the beginning, has limited usages owing to its bubbly properties and low thermostabilities. Therefore, the sulfonium salts described in the following Patent document No. 2 have been used widely, but nowadays, iodonium salts, which don't release benzene, are used as U.V. curable ink for foods-packaging medium, since a small amount of benzene is released from the sulfonium salt type photo-polymerizing initiator as described in the following Non-patent document No. 1

Patent document No. 2: Japanese Patent Application Laid-open No. 2001-288205

Non-patent document No. 1: Material Stage Vol. 2, No. 2.2002.

However, the iodonium salt described above has a disadvantage such as too short preservative period in summer owing to its low thermostability. Its curability(sensitivity) is also not so good.

Therefore, the object of the present invention is to provide a novel compound useful as a suitable photo-polymerizing initiator being able to give a rapidly and good cured article by effective absorption of the radiation from the source of a ray, a photo-acid generator comprising the novel compound and a photo-polymerizable compositions comprising the same.

And another object of the present invention is to provide a stereolithographic resin composition, by which the above mentioned disadvantages of the prior art can be overcome, the prevention of curing under oxygen do not occur and a molding with desirable dimension can be obtained easily, having sufficient sensitivity to an energy beam to be exposed and to provide a stertlithographic process using the resin composition.

Furthermore, another object of the present invention is to provide a photo-polymerizable composition, which can be used for wide usage, such as an ink for foods-packaging medium, and has improved thermostability and curability (sensitivity), a photo-acid generator, which is useful as photo-polymerizing initiator for such composition, novel aromatic sulfonium salt compound for such photo-acid generator, and U.V. curable ink using the compound.

DISCLOSURE OF THE INVENTION

The inventors have, after thorough study, succeeded to synthesize the novel aromatic sulfonium salt compound of the following general formula (I), and have found that the compound is activated by effective absorption of long-wave radiation, therefore, the photo-polymerizable composition comprising the said compound can be cured rapidly to give good cured articles, without the production of benzene and also the photo-resist comprising the same has good sensitivity and good resolution, to finally complete the present invention.

Further, the inventors have found that, when a stereolithographic resin composition comprising an aromatic sulfonium salt compound of the following general formula (I) as an energy beam sensitive cationic polymerizing initiator, with a cationically polymerizing organic substance is applied to stereolithographic process by exposing to a certain specific energy beam, this resin composition do not suffer from the hindrance to curing by oxygen, can easily give shaped articles having desired sizes by virtue of the high accuracy thereof in curing, owing to the high sensitivity thereof for radiant energy, to finally complete the present invention.

That is, the present invention is an aromatic sulfonium salt compound expressed by a general formula(I),

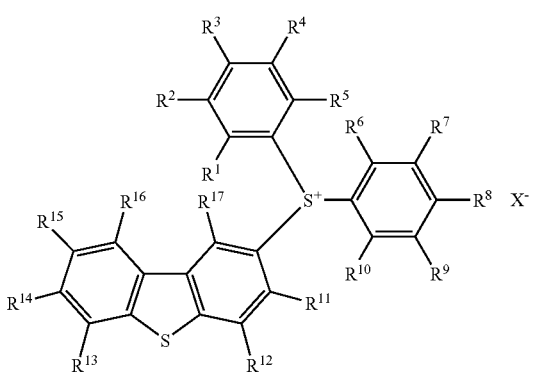

(I)

wherein, $R^1$ to $R^{17}$ are identical or different, respectively a group selected from the group consisting of hydrogen, halogen, nitro, hydroxyl, alkyl, alkoxy, acyl, phenoxy, ester, aryl, thioether, thiocarbonyl, sulfinyl, sulfonyl, amino, amide, imide, nitrile, phosphino, phosphonio, phosphoryl and fluoroalkyl group of 1-8 carbon atoms, wherein the moieties other than functional groups of these groups can be saturated aliphatic hydrocarbons, unsaturated aliphatic hydrocarbons, alicyclic hydrocarbons, carbocyclic aromatic hydrocarbons or heterocyclic hydrocarbons of 1-12 carbon atoms, and $R^5$ and $R^6$ can be condensed together with to form a covalent bond, X is an atomic group, which can form a monovalent anion.

In the aromatic sulfonium salt compound of the present invention, the acyl group in the compound of above-mentioned general formula (I) is preferably R—CO—, or Ar—CO—, wherein R is alkyl group having straight chain or branched chain or alicyclic hydrocarbon group, Ar is

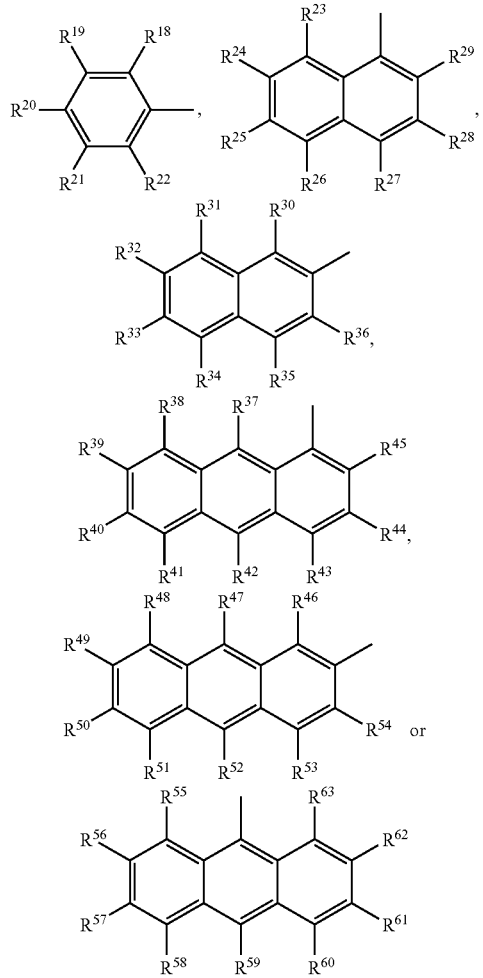

and $R^{18}$ to $R^{63}$ are identical or different, hydrogen, halogen, hydroxyl, alkyl or alkoxy group.

According to the present invention, in the above general formula (I), $X^-$ is an atomic group, which can form a monovalent anion. In the aromatic sulfonium salt compound of the present invention, $X^-$ is preferably selected from the group consisting of $SbF_6^-$, $PF_6^-$, $AsF_6^-$, $BF_4^-$, $SbCl_6^-$, $ClO_4^-$, $CF_3SO_3^-$, $CH_3SO_3^-$, $FSO_3^-$, $F_2PO_2^-$, p-toluene sulfonate, camphor sulfonate, nonafluorobutane sulfonate, hexadecafluorooctane sulfonate and tetraaryl borate.

Examples of tetraaryl borate include tetraphenyl borate and its derivatives, which at least one hydrogen on the phenyl group is substituted by alkyl group, halogen, halogenated alkyl group, hydroxy alkyl group, alkoxyl group, phenyl group, alkoxycarbonyl group, and are preferably tetrakis (pentafluorophenyl) borate, tetrakis (4-fluorophenyl) borate and tetraphenyl borate.

The present invention is also a photo-acid generator comprising the aforementioned aromatic sulfonium salt compound.

Furthermore, the present invention is a photo-polymerizable composition comprising, (1) cationically polymerizing organic substance, and (2) photo-acid generator mentioned above as an energy beam sensitive cationic polymerizing initiator.

In addition, the present invention is a photo-polymerizable composition additionally comprising, (3) radically polymerizing organic substance, and (4) energy beam sensitive radical polymerizing initiator as essential components.

In the present invention, at least one among the (1) cationically polymerizing organic substance is aforementioned photo-polymerizable composition, which is an organic compound containing one or more epoxy group in a molecule.

In addition, the present invention is a photo-polymerizable composition, which comprises a compound having a cyclohexenoxide structure in a molecule at the content of 30% by weight or more based on the (1) cationically polymerizing organic substance.

In addition, the present invention is a photo-polymerizable composition, which comprises a compound having (meth) acrylic group in a molecule at the content of 50% by weight or more based on the (3) radically polymerizing organic substance.

In the photo-polymerizable composition of the present invention, (5) organic compound having two or more hydroxyl groups in a molecule, (6) thermoplastic polymer compound, and the like may be added as optional components.

In addition, the present invention is an aromatic sulfonium salt compound, wherein at least one of $R^1$ to $R^{17}$ in the above general formula (I) is acyl group, which have a good curability to give a good cured articles.

In addition, the present invention is a photo-acid generator comprising the aforementioned aromatic sulfonium salt compound, and the present invention is also a photo-polymerizable composition comprising the aforementioned photo-acid generator, and furthermore, the present invention is a stereolithografic resin composition comprising such a photo-polymerizable composition.

Still furthermore, the present invention is a stereolithographic process, wherein a given portion of the aforementioned stereolithographic resin composition is exposed to the beam in order to produce a desired thickness of cured layer, the energy of the beam with an emission wave length of 345 to 360 nm being not less than 70% based on the total energy of the beam with an emission wave length of 250 to 400 nm to cure the exposed portion thereof; then, the cured layer is overlaid with another layer of the stereolithographic resin composition, which is then cured in the same manner to produce a second cured layer which continuously overlaps the first layer; and the same process is repeated to finally obtain a three-dimensional molding.

In addition, the present invention is an aromatic sulfonium salt compound, which does not release benzene when exposed to beam, expressed by a general formula (I).

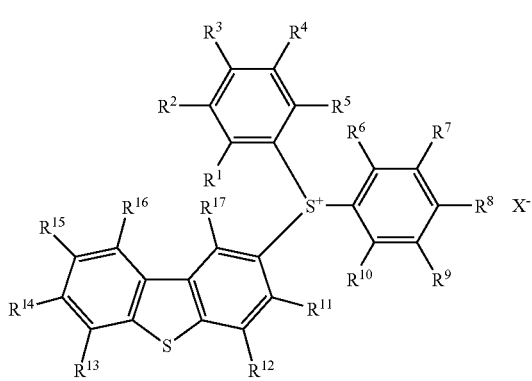

(I)

wherein, $R^1$ to $R^{17}$ are identical or different, respectively a group selected from hydrogen, halogen, nitro, hydroxyl, alkyl, alkoxy, acyl, phenoxy, ester, aryl, thioether, thiocarbonyl, sulfinyl, sulfonyl, amino, amide, imide, nitrile, phosphino, phosphonio, phosphoryl and fluoroalkyl groups of 1-8 carbon atoms, wherein the moiety other than the functional groups of these groups may be saturated aliphatic hydrocarbon, unsaturated aliphatic hydrocarbon, alicyclic hydrocarbon, carbocyclic aromatic hydrocarbon or heterocyclic aromatic hydrocarbon of 1-12 carbon atoms, and $R^5$ and $R^6$ can be condensed together with to form a covalent bond, provided that $R^1$ to $R^5$ are not all hydrogen at the same time, and that $R^6$ to $R^{10}$ are not all hydrogen at the same time, X is the same above. And the present invention is a photo-acid generator comprising the aromatic sulfonium salt compound, and the present invention is also a photo-polymerezable composition comprising the photo-polymerizable initiator, which comprises the aforementioned photo-acid generator.

In addition, the present invention is related to an U.V. curable ink for foods-packaging medium comprising the aforementioned photo-polymerizable composition as well as an U.V. curable ink comprising the aforementioned photo-polymerizable composition, and consequently, according to the present invention, a packaging medium for foods, which is printed with an U.V. curable ink for foods-packaging medium, is constructed.

BEST MODE FOR CARRYING OUT THE INVENTION

Figure 1:
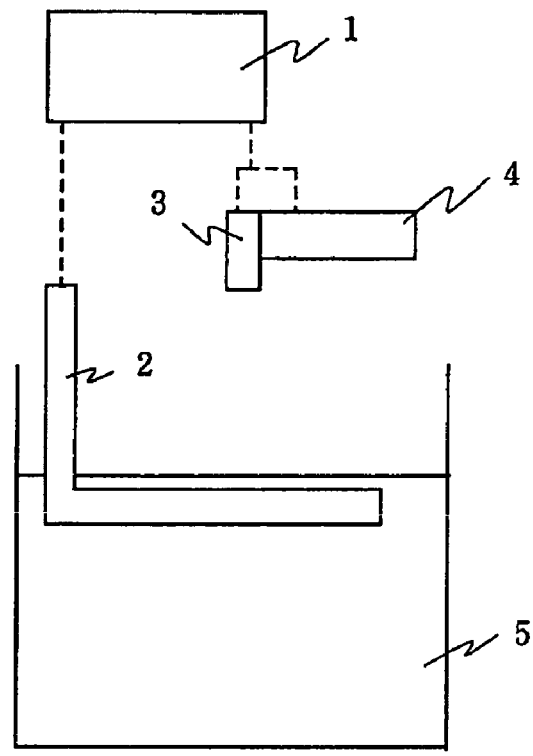
FIG. 1 is an illustration of a step to form a layer of uncured resin in the stereolithographic process.

The concrete embodiments of the present invention will be illustrated in detail below.

In the general formula (I) mentioned above, preferable $R^1$~$R^{10}$ group include, identical or different, respectively hydrogen, halogen, nitro, hydroxyl, alkyl, alkoxy, acyl or fluoroalkyl group having 1 to 8 of carbon atoms. $R^5$ and $R^6$ can be condensed together to form a covalent bond. Examples of halogen atoms include fluorine, chlorine, bromine and iodine, but fluorine is the best owing to its good energy beam sensitivity. Examples of alkyl group include methyl, ethyl, propyl, isopropyl, butyl, isobutyl, tert-butyl, pentyl, isopentyl, tert-pentyl, neopentyl, hexyl, iso-hexyl, heptyl, octyl, 2-ethylhexyl, nonyl, decyl, undecyl, dodecyl, tridecyl, isotridecyl, myristyl, palmityl and stearyl group. Alkyl groups of 1 to 4 carbon atoms are preferable, methyl and ethyl group are especially preferable. Examples of alkoxy group include methoxy, ethoxy, propyloxy, butyloxy, pentyloxy, hexyloxy, heptyloxy, octyloxy, nonyloxy, decyloxy, undecyloxy, dodecyloxy, tridecyloxy, myristyloxy, palmityloxy and stearyloxy group. Alkoxy groups of 1 to 4 carbon atoms are preferable, methoxy and ethoxy group are especially preferable. Examples of fluoroalkyl group include fluoromethyl, difluoromethyl, trifluoromethyl, difluoroethyl and perfluoroethyl group, and trifluoromethyl group is especially preferable.

Acyl group includes R—CO— or Ar—CO—. R group includes a straight or a branched alkyl group, or an alicyclic hydrocarbon group.

Ar group includes

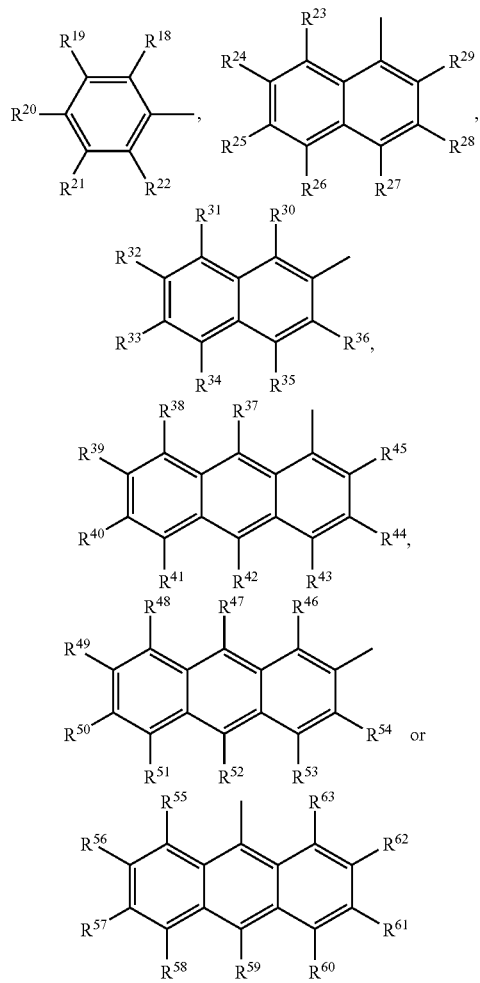

wherein $R^{18}$ to $R^{63}$ are identical or different, respectively hydrogen, halogen, hydroxyl, alkyl or alkoxy groups.

Examples of R mentioned above, include methyl, ethyl, propyl, isopropyl, butyl, isobutyl, t-butyl, pentyl, isopentyl, t-pentyl, neopentyl, hexyl, ioshexyl, heptyl, octyl, 2-ethylhexyl, nonyl, decyl, undecyl, dodecyl, tridecyl, isotridecyl, myristyl, palmityl, stearyl, cyclopentyl and cyclohexyl group.

Examples of $R^{18}$ to $R^{63}$ for Ar group, include fluorine, chlorine, bromine and iodine in halogen. Examples of alkyl groups include methyl, ethyl, propyl, isopropyl, butyl, isobutyl, t-butyl, pentyl, isopentyl, t-pentyl, neopentyl, hexyl, isohexyl, heptyl, octyl, 2-ethylhexyl, nonyl, decyl, undecyl, dodecyl, tridecyl, isotridecyl, myristyl, palmityl and stearyl group. Examples of alkoxy groups include methoxy, ethoxy, propyloxy, butyloxy, pentyloxy, hexyloxy, heptyloxy, octyloxy, nonyloxy, decyloxy, undecyloxy, dodecyloxy, tridecyloxy, myristyloxy, palmityloxy and stearyloxy group.

Such groups described above are identical or different, and it is preferable that all of $R^1$ to $R^{10}$ are hydrogen, or any group of $R^1$ to $R^5$ except for one or two (more preferably one) of them are hydrogen and any group of $R^6$ to $R^{10}$ except for one or two (more preferably one) of them are hydrogen. Or, it is more preferable that all of $R^1$ to $R^{10}$ are hydrogen, or any group of $R^1$ to $R^5$ except for one of them are hydrogen, wherein such one group may be selected from methyl, fluoro, nitro or acyl group, and any group of $R^6$ to $R^{10}$ except for one of them are hydrogen, wherein such one group may be selected from methyl, fluoro, nitro or acyl group. It is also preferable that $R^5$ and $R^6$ are condensed together with to form a covalent bond.

The group $R^{11} \sim R^{17}$ are similar to $R^1 \sim R^{10}$ described above (except for the case of that $R^5$ and $R^6$ are condensed together with to form a covalent bond). Especially, it is particularly preferable that any group of them is hydrogen except for one group which is Ar—CO—. The typical example of such aromatic sulfonium salt compound is shown as formula (II),

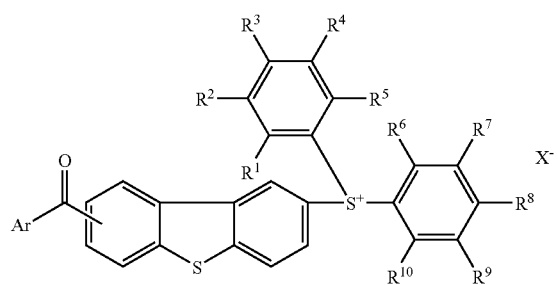

(II)

wherein $R^1 \sim R^{10}$ and Ar are described above. Particularly preferable Ar group is phenyl or tolyl group.

The preferable examples of aromatic sulfonium salt compound (as for cationic moieties) of the present invention are shown as follows,

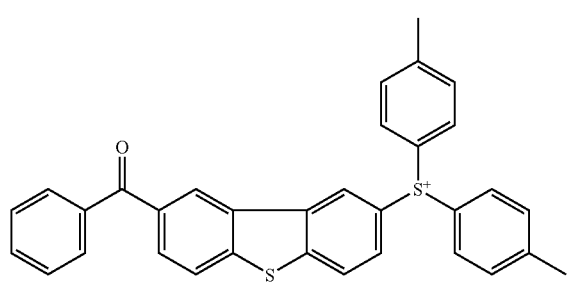

-continued

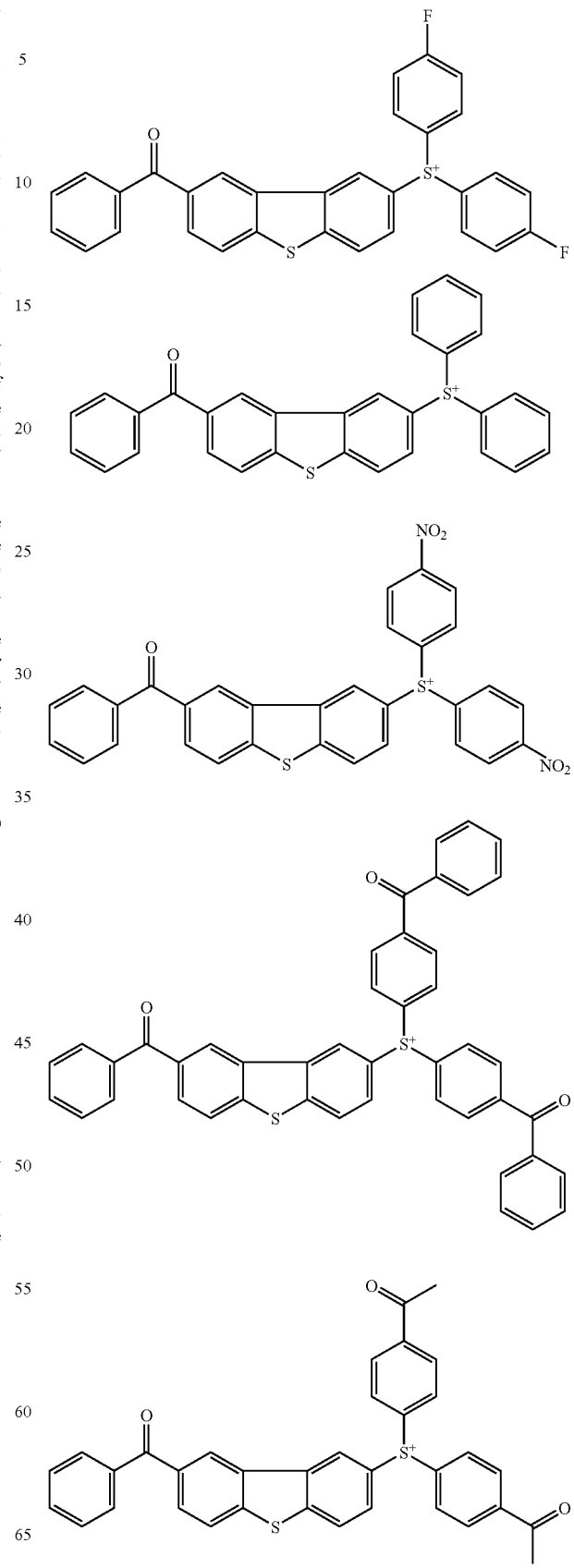

-continued

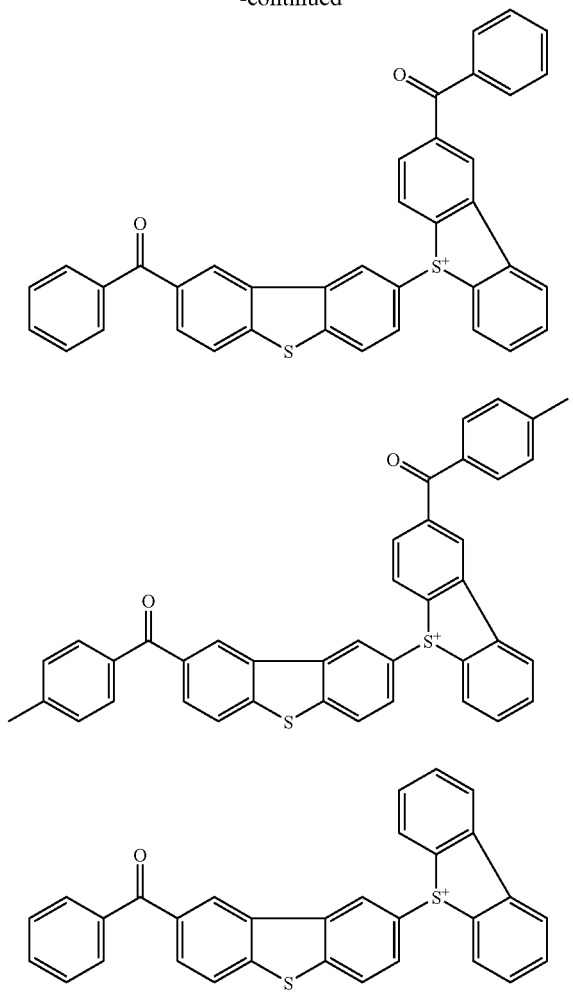

Particularly preferable examples of anion parts in the aromatic sulfonium salt compound of the present invention are $SbF_6^-$ and $PF_6^-$.

In the case of the compound shown by formula (II), in which $R^1$ to $R^{10}$ are hydrogen and Ar is phenyl group, the mentioned compound can be produced by reacting dibenzothiophene with benzoyl chloride to obtain a benzoyl dibenzothiophene and reacting the resulting product with substituted or non-substituted diphenyl sulfoxide, for example, in sulfuric acid, followed by exchange of the salts.

Since the photo-acid followed by exchange of the salts, for example in generator of the present invention has the character to release, in situ, a Lewis acid by being exposed to an active energy beam of an ultraviolet ray, an electron beam, an X-ray, a radioactive ray, or a high-frequency wave, the photo-acid generator can initiate polymerization of a cationically polymerising organic substance. Therefore, the photo-acid generator of the present invention is useful for cationic photo-polymerizing initiator.

And the photo-acid generator of the present invention has the sensitivity to longer wave radiation compared with the customary aromatic sulfonium salt, thus can effectively absorb the beam with an emission wave length of 365 nm, which is the brightest beam from high-pressure mercury-vapor lamp among general sources of light. Therefore, cationically polymerising composition or photo-resist, which contains the aromatic sulfonium salt compound of the present invention has greatly improved sensitivity, compared with cationically polymerising composition or photo-resist, which contains the previous aromatic sulfonium salt compound.

In the compound expressed by a general formula (I), which does not release benzene when photo-acid is generated, $R^1$ to $R^5$ are selected from hydrogen, halogen(preferably F or Cl), hydroxyl, alkyl (preferably straight chain or branched chain having carbon number 1 to 4), alkoxy (preferably alkoxy having carbon number 1 to 6), acyl and the like, more preferably hydrogen, alkyl, alkoxy and acyl, particularly preferably sum of carbon number of $R^1$ to $R^5$ is 1 to 8. The combination of these groups is optional, and identical or different, if the groups are not all hydrogen at the same time.

$R^6$ to $R^{10}$ are selected from hydrogen, halogen(preferably F or Cl), hydroxyl, alkyl (preferably straight chain or branched chain having carbon number 1 to 4), alkoxy (preferably alkoxy having carbon number 1 to 6), acyl and the like, more preferably hydrogen, alkyl, alkoxy and acyl group, particularly preferably sum of carbon number of $R^6$ to $R^{10}$ is 1 to 8. The combination of these groups is optional, and identical or different, if the groups are not all hydrogen at the same time. It is also preferable that $R^5$ and $R^6$ may be condensed together with to form a covalent bond.

The preferable examples of aromatic sulfonium salt compound of the said present invention are shown as follows,

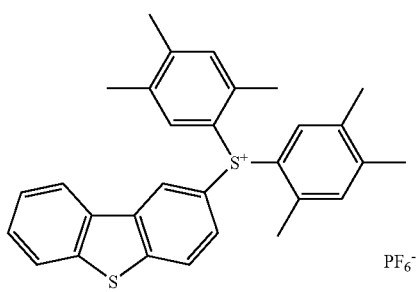

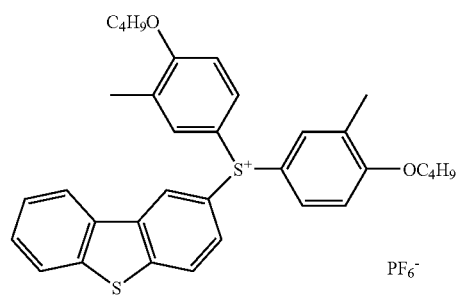

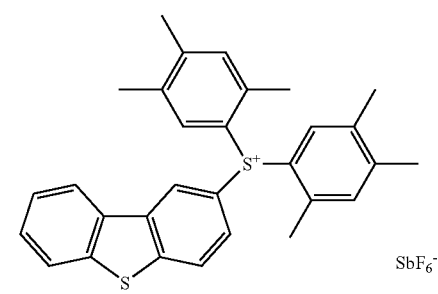

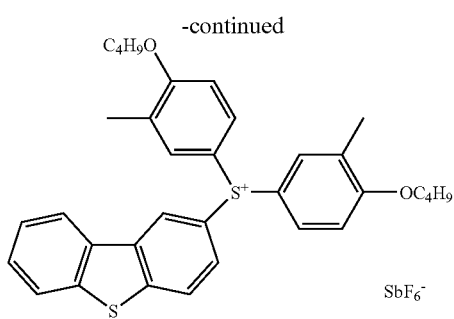

The aforementioned compounds can be produced, for example, by exchange of the salts after preparing the sulfonium salts by condensation with dehydration of a dibenzothiophens with a substituted diphenyl sulfoxide in sulfuric acid.

Furthermore, among the aromatic sulfonium salt compounds, shown at page 17, 18 herein, such compounds except for ones that all of $R^1$ to $R^{10}$ are hydrogen are preferable.

The photo-acid generator of the present invention do not release benzene, when generate acid by being exposed to an energy beam, as well as the iodoniuum salt, which have been used for ink of foods packaging medium. Furthermore, the photo-acid has improved performance in thermo-stability and curability (sensitivity) compared with the iodoniuum salt.

(1) Cationically polymerizing organic substance, which is one component of photo-polymerizable composition of the present invention, is a compound which polymerizes or crosslinks by cationic polymerizing initiator which is activated by exposure to light.

Examples of such compounds include epoxy compounds, oxetane compounds, cyclic lactone compounds, cyclic acetal compounds, cyclic thioether compounds, spiroorthoester compounds, vinyl compounds, and the like. They may be used independently or in combination. Among them, epoxy compounds are suited, for their availability and ease of handling. As such epoxy compounds, aromatic, alicyclic and aliphatic epoxy compounds are suited.

Further, examples of the alicyclic epoxy resins described above, include polyglycidyl ethers of poly-hydric alcohols having at least one alicyclic ring, or a compound containing cyclohexane-oxide or cyclopentene-oxide obtained by epoxidation of a compound having a structure of cyclohexene- or cyclopentene-ring with oxidant. For example, mention may be made of diglycidyl ether of hydrogenated bisphenol A, 3,4-epoxycyclohexylmethyl-3,4-epoxycyclohexane carboxylate, 3,4-epoxy-1-methylcyclohexyl-3,4-epoxy-1-methylhexane carboxylate, 6-methyl-3,4-epoxycyclohexylmethyl-6-methyl-3,4-epoxycyclohexane carboxylate, 3,4-epoxy-3-methylcyclohexylmethyl-3,4-epoxy-3-methylcyclohexane carboxylate, 3,4-epoxy-5-methylcyclohexylmethyl-3,4-epoxy-5-methylcyclohexane carboxylate, 2-(3,4-epoxycyclohexyl-5,5-spiro-3,4-epoxy) cyclohexane-methadioxane, bis(3,4-epoxycyclohexylmethyl)adipate, 3,4-epoxy-6-methylcyclohexyl carboxylate, methylene bis(3,4-epoxycyclohexane), dicyclopentadiene diepoxide, ethylene bis(3,4-epoxycyclohexane carboxylate), dioctyl epoxyhexahydrophthalate, di-2-ethylhexyl epoxyhexahydrophthalate, and the like.

As the alicyclic epoxy resins described above, suitable products available commercially include UVR-6100, UVR-6105, UVR-6110, UVR-6128, UVR-6200, (from Union Carbide Co.,), Celoxide2021, Celoxide2021P, Celoxide2081, Celoxide2083, Celoxide2085, Celoxide2000, Celoxide3000, CyclomerA200, CyclomerM100, CyclomerM101, EpoleadGT-301, EpoleadGT-302, Epolead-401, Epolead-403, ETHB, EpoleadHD300, (from Daicel Chemical Industries, LTD.), KRM-2110, KRM-2199, (from Asahi Denka Kogyo Co. Ltd.).

Among the alicyclic epoxy resins, the epoxy resins having the structure of cyclo-hexene oxide exhibits preferable curing performance (fast curing).

Examples of the aromatic epoxy resins described above, include polyglycidyl ethers of polyhydric phenols having at least one aromatic ring, or their adducts with alkylene oxide, such as glycidyl ethers of bisphenol A, bisphenol F or their adducts with alkylene oxides, or epoxy-novolac resins.

And also, examples of the aliphatic epoxy resins described above, include polyglycidyl ethers of aliphatic polyhydric alcohols or their alkylene oxide adducts, polyglycidyl esters of aliphatic, long chain, poly-basic acids, homopolymers of glycidyl acrylate or methacrylate prepared by vinyl polymerization, copolymers of glycidyl acrylate or methacrylate, prepared by vinyl polymerization with other vinyl monomer and the like. Typical examples of such compounds include glycidyl ethers of polyhydric alcohols, such as 1,4-butanediol diglycidyl ether, 1,6-hexanediol diglycidyl ether, triglycidyl ether of glycerol, triglycidyl ether of trimethylol propane, tetraglycidyl ether of sorbitol, hexaglycidyl ether of dipentaerythritol, diglycidyl ether of polyethylene glycol, and diglycidyl ether of polypropylene glycol; polyglycidyl ethers of polyether-polyols, which can be obtained by adding one or more alkylene oxides with aliphatic polyhydric alcohols such as propylene glycol, trimethylol propane and glycerol; and diglycidyl esters of aliphatic, long chain di-basic acids. Further, mention may be made of mono-glycidyl ethers of aliphatic higher alcohols; mono-glycidyl ethers of phenol, cresol, butyl phenol, or polyether alcohols which can be obtained by adding alkylene oxide thereto; glycidyl esters of higher fatty acids; epoxidized soybean oil; octyl epoxy-stearate; butyl epoxy-stearate; epoxidized soybean oil; epoxidized polybutadiene and the like.

As the aromatic and aliphatic epoxy resins described above, suitable products available commercially include Epicoat801, Epicoat828, (from Yuka-Shell-Epoxy Co.), PY-306, 0163, DY-022, from Ciba-Geigy Co.), KRM-2720, EP-4100, EP-4000, EP-4080, EP-4900, ED-505, ED-506, (from Asahi Denka Kogyo Co. Ltd.). Epolight M-1230, Epolight EHDG-L, Epolight 40E, Epolight 100E, Epolight 200E, Epolight 400E, Epolight 70P, Epolight 200P, Epolight 400P, Epolight 1500NP, Epolight 1600, Epolight 80MF, Epolight 100MF, Epolight 4000, Epolight 3002, Epolight FR-1500, (from Kyoeisha Chemical Co., Ltd.). Santoto ST0000, YD-716, YH-300, PG-202, PG-207, YD-172, YDPN638, (from Tohto Kasei Co, Ltd.)

Examples of the oxetane compounds described above, include 3-ethyl-3-hydroxymethyloxetane, 3-(meta)allyloxymethyl-3-ethyloxetane, (3-ethyl-3-oxetanylmethoxy) methylbenzene, 4-fluoro-[1-(3-ethyl-3-oxetanylmethoxy) methyl] benzene, 4-methoxy-[1-(3-ethyl-3-oxetanylmethoxy)methyl] benzene, [1-(3-ethyl-3-oxetanylmethoxy)ethyl] phenylether, isobutoxymethyl(3-ethyl-3-oxetanylmethyl) ether, isobornyloxyehtyl(3-ethyl-3-oxetanylmethyl) ether, isobornyl (3-ethyl-3-oxetanylmethyl) ether, 2-ethylhexyl (3-ethyl-3-oxetanylmethyl) ether, ethyldiethyleneglycol (3-ethyl-3-oxetanylmethyl) ether, dicyclopentadiene(3-ethyl-3-oxetanylmethyl) ether, dicyclopentenyloxyethyl (3-ethyl-3-oxetanylmethyl) ether, dicyclopentenyl(3-ethyl-3-oxetanylmethyl) ether, tetrahydrofurfuryl(3-ethyl-3-oxetanylmethyl) ether, tetrabromophenyl(3-ethyl-3-oxetanylmethyl) ether, 2-tetrabromophenoxyethyl(3-ethyl-3-oxetanylmethyl) ether, tribromophenyl(3-ethyl-3-oxetanylmethyl) ether, 2-tribromophenoxyethyl(3-ethyl-3-oxetanylmethyl) ether, 2-hydroxyethyl(3-ethyl-3-oxetanylmethyl) ether, 2-hydroxypropyl(3-ethyl-3-oxetanylmethyl) ether, butoxyethyl(3-ethyl-3-oxetanylmethyl) ether, pentachlorophenyl(3-ethyl-3-oxetanylmethyl) ether, pentabromophenyl(3-ethyl-3-oxetanylmethyl) ether, bornyl(3-ethyl-3-oxetanylmethyl) ether, 3,7-bis(3-oxetanyl)-5-oxa-nonane, 3,3'-(1,3,-(2-methylenyl)propanediyl bis(oxymethylene))bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethyleneglycolbis(3-ethyl-3-oxetanylmethyl) ether, dicyclopentenylbis(3-ethyl-3-oxetanylmethyl) ether, triethyleneglycolbis(3-ethyl-3-oxetanylmethyl) ether, tetraethyleneglycolbis(3-ethyl-3-oxetanylmethyl) ether, tricyclodecanediyldimethylene(3-ethyl-3-oxetanylmethyl) ether, trimethylolpropanetris(3-ethyl-3-oxetanylmethyl) ether, 1,4-bis(3-ethyl-3-oxetanylmethoxy) butane, 1,6-bis(3-ethyl-3-oxetanylmethoxy) hexane, pentaerythritoltris(3-ethyl-3-oxetanylmethyl) ether, pentaerythritoltetrakis(3-ethyl-3-oxetanylmethyl) ether, polyethyleneglycolbis (3-ethyl-3-oxetanylmethyl) ether, dipentaerythritolhexakis(3-ethyl-3-oxetanylmethyl) ether, dipentaerythritolpentakis(3-ethyl-3-oxetanylmethyl) ether, dipentaerythritoltetrakis(3-ethyl-3-oxetanylmethyl) ether, caprolactone modified dipentaerythritolhexakis(3-ethyl-3-oxetanylmethyl) ether, caprolactone modified dipentaerythritolpentakis(3-ethyl-3-oxetanylmethyl) ether, ditrimethylolpropanetetrakis(3-ethyl-3-oxetanylmethyl) ether, ethyleneoxidemodifiedbisphenolAbis(3-ethyl-3-oxetanylmethyl) ether, propyleneoxide modified bisphenolAbis(3-ethyl-3-oxetanylmethyl) ether, ethyleneoxide modified bisphenolA, which is reduced by hydrogen, bis(3-ethyl-3-oxetanylmethyl) ether, propyleneoxide modified bisphenolA, which is reduced by hydrogen, bis(3-ethyl-3-oxetanylmethyl) ether, ethyleneoxide modified bisphenolF(3-ethyl-3-oxetanylmethyl) ether, and the like. These compounds may be used independently or in combination. These oxetane derivatives may be used preferably to effect flexible property for the molding.

The cationically polymerizing organic substances, which are described above as components of photo-polymerizable composition, can be applied as well as (1) cationically polymerizing organic substances used in the stereolithografic resin composition of the present invention.

Furthermore, it is particularly preferable to employ an epoxy compound having cyclohexene oxide structure in a molecule among the epoxy compounds described above in an amount of 30% by weight or more based on cationically polymerizing organic substances to effect good curing performance (curing rate) and moldings at high precision, as the stereolithaphic resin composition. As 70% or less by weight of the cationically polymerizing organic substances, use may be made of epoxy compound except for the one mentioned above or a cationically polymerizing organic substance except for epoxy compounds, as listed below. And also, it is preferable to employ the mixture of the cationically polymerizing organic substances except for epoxy compounds and the cyclohexen oxide compound mentioned above.

Examples of cationically polymerizing organic substances except for epoxy compounds, which can be employ in this invention, include oxetane compounds described above; oxorane compounds such as tetrahydrofuran and 2,3-dimethyl-tetrahydrofuran; cyclic acetal compounds such as trioxane, 1,3-dioxorane and 1,3,6-trioxan-cyclooctane; thiirane lactones such as β-propiolactone and ε-caprolactone; thiirane compounds such as ethylene sulfide and thioepichlorohydrine; thietane compounds such as 1,3-propine sulfide and 3,3-dimethyl thietane; cyclic thio-ether compounds such as tetrahydro-thiophene derivatives; vinyl ether compounds such as ethylene glycol divinyl ether, alkyl vinylether, 2-chloroethyl vinylether, 2-hydroxyethyl vinyl ether, triethyleneglycol divinyl ether, 1,4-cyclohexane dimethanol divinyl ether, hydroxybutyl vinyl ether, propenyl ether of propyleneglycol; spiro-ortho ester compounds obtained by the reaction of epoxy compounds with lactones; ethylenic unsaturated compounds such as styrene, vinyl cyclohexene, iso-butylene and polybutadiene, and the derivatives thereof.

In the stereolithographic resin composition, it is preferable to employ the oxetane compound as the cationically polymerizing organic substance at the content of 30% by weight or more based on total cationically polymerizing organic substances to effect flexible property for the molding. As the remaining cationically polymerizing organic substances at the content of not more than 70% by weight, mention may be made of the aforementioned cationically polymerizing organic substances except for the oxetane compounds such as epoxy resin or the like.

According to the present invention, as (1) cationically polymerizing organic substance, the cationically polymerizing organic substances described above can be used independently or in combination.

As photo-polymerizing initiator, a photo-acid generator can be used without limitation in the customary range of use, however, a photo-acid generator is preferably used at the content of 0.05 to 10 parts by weight based on the 100 parts by weight of the cationically polymerizing organic substance. But, according to the performance of the cationically polymerizing organic substance, the intensity of the beam to be exposed, period to be cured and the cost factor, it can be used out of range described above.

The radically polymerizable photo-polymerizing composition such as acrylic resin and unsaturated polyester can be used mixing with the photo-polymerizable composition of the present invention.

If desired, or if necessary, a photosensitizer, such as anthracene derivative or pyrene derivative, thermosensitive cationic polymerizing initiator, filler, diluent, solvent, pigment, flexibilizer, defoamer, leveling agent, thickener, stabilizer, flame retardant, antioxidant, may be added in the stereolithographic resin composition of the present invention.

The photo-polymerizing composition of the present invention is useful for wide application, for example manufacturing of printing plate for litho printing or relief printing, photoresist for manufacturing of printed board, IC and LSI, image processing such as relief image and printed image copy, photo-curable ink, coating or adhesives etc.

In the case of the stereolithographic resin composition of the present invention, the aforementioned (2) energy beam sensitive cationic polymerizing initiator can be used preferably at the content of 0.05 to 10% by weight, more preferably at the content of 0.1 to 10% by weight based on the (1) cationically polymerizing organic substance. When the content exceeds this range, the cured articles have insufficient strength, and in the case of below the cure of the resin is insufficient.

(3) Radically polymerizing organic substance, which is used as the photo-polymerizable resin composition of the present invention, is a radically polymerizing organic substance which polymerizes or cross-links upon exposure to an energy beam in the presence of a energy beam sensitive radical polymerizing initiator and, preferably, has at least one unsaturated double bond per one molecule.

Examples of such compounds include acrylate compounds, methacrylate compounds, allyl urethane compounds, unsaturated polyester compounds, and styrene series compounds.

Among these radically polymerizing organic substances, those having (meth)acrylic groups, such as epoxy (meth)acrylates, urethane (meth)acrylates, polyester (meth)acrylates, polyether (meth)acrylates, (meth)acrylic esters of alcohols, are best suited, for their availability and ease of synthesis and handling.

Here, epoxy (meth)acrylates refer to acrylates which are obtained by the reaction of, for example, a known aromatic, alicyclic or aliphatic epoxy resin and (meth)acrylic acid. The most preferable of these epoxy (meth)acrylates are the (meth)acrylates of aromatic epoxy resins which are obtained by the reaction of a polyglycidyl ether of a polyhydric phenol having at least one aromatic nuclei or an added alkylene oxide thereof, and (meth)acrylic acid. One example is the (meth)acrylate obtained by the reaction of a glycidyl ether and (meth)acrylic acid, the former obtained by the reaction of bisphenol A or an added alkylene oxide thereof and epichlorohydrin. Another example is the (meth) acrylate obtained by the reaction of an epoxy novolac resin and (meth)acrylic acid.

The most preferable urethane (meth)acrylates are those obtained by the reaction of one or more hydroxyl-containing polyesters or polyethers, a hydroxyl-containing(meth)acrylic ester, and an isocyanate, and those obtained by the reaction of a hydroxyl-containing(meth)acrylic ester and an isocyanate.

Among hydroxyl-containing polyesters, the most preferable ones are those obtained by the reaction of one or more aliphatic polyhydric alcohols and one or more polybasic acids. Examples of the aliphatic polyhydric alcohols include 1,3-butanediol, 1,4-butanediol, 1,6-hexanediol, diethylene glycol, triethylene glycol, neopentyl glycol, polyethylene glycol, polypropylene glycol, trimethylolpropane, glycerol, pentaerythritol, and dipentaerythritol. Examples of the polybasic acids include adipic acid, terephthalic acid, phthalic anhydride, and trimellitic acid.

Among hydroxyl-containing polyethers, the most preferable ones are those obtained by adding one or more alkylene oxides to a aliphatic polyhydric alcohol. Examples of the aliphatic polyhydric alcohols are such as those listed above. Examples of the alkylene oxides include ethylene oxide and propylene oxide.

Among hydroxyl-containing (meth)acrylic esters, the most preferable ones are those obtained by the esterification of an aliphatic polyhydric alcohol and (meth)acrylic acid. Examples of the aliphatic polyhydric alcohols are such as those listed above.

The best suited of these hydroxyl-containing (meth)acrylic esters are those obtained by the esterification of a aliphatic dihydric alcohol and (meth)acrylic acid, such as 2-hydroxyethyl (meth)acrylate.

Among isocyanates, the most preferable ones are those having one or more isocyanic group in a molecule, particularly divalent isocyanic compounds such as tolylene diisocyanate, hexamethylene diisocyanate, and isophorone diisocyanate.

The most preferable polyester (meth)acrylates are those obtained by the reaction of a hydroxyl-containing and (meth)acrylic acid. Among hydroxyl-containing polyesters, the most preferable ones are those obtained by the esterification of one or more aliphatic polyhydric alcohols and one or more monobasic acids, polybasic acids and phenols. Examples of the aliphatic polyhydric alcohols are such as those listed above. Examples of the monobasic acids formic acid, acetic acid, butyl carbonic acid, and benzoic acid. Examples of the polybasic acids include adipic acid, terephthalic acid, phthalic anhydride, and trimellitic acid. Examples of the phenols include phenol, p-nonyl phenol, bisphenol A, and the like. The most preferable polyether (meth)acrylates are those obtained by the reaction of a hydroxyl-containing polyether and (meth)acrylic acid. Among hydroxyl-containing polyethers, the most preferable ones are those obtained by adding one or more alkylene oxides to an aliphatic polyhydric alcohol. Examples of the aliphatic polyhydric alcohols are such as those listed above. Examples of the alkylene oxides include ethylene oxide, propylene oxide and the like.

The most preferable (meth)acrylic esters of alcohols are (meth)acrylates obtained by the reaction of an aromatic or aliphatic alcohol having at least one hydroxyl group in a molecule or an added alkylene oxide thereof, and (meth)acrylic acid. Examples of such (meth)acrylates include 2-ethylhexyl (meth)acrylate, 2-hydroxyethyl (meth)acrylate, 2-hydroxypropyl (meth)acrylate, isoamyl (meth)acrylate, lauryl (meth)acrylate, stearyl (meth)acrylate, isooctyl (meth)acrylate, tetrahydrofurfuryl (meth)acrylate, isobonyl (meth)acrylate, benzyl (meth)acrylate, 1,3-butanediol di(meth)acrylate, 1,4-butanediol di(meth)acrylate, 1,6-hexanediol di(meth)acrylate, diethylene glycol di(meth)acrylate, triethylene glycol di(meth)acrylate, neopentyl glycol di(meth)acrylate, polyethylene glycol di(meth)acrylates, polypropylene glycol di(meth)acrylates, trimethylolpropane tri(meth)acrylate, pentaerythritol tetra (meth)acrylate, dipentaerythritol hexa(meth)acrylate, and $\epsilon$-caprolactone-modified dipentaerythritol hexa(meth)acrylate.

Among these (meth)acrylate, poly(meth)acrylate of polyhydric alcohols are particularly preferable.

As the radically polymerizing organic substance described above, suitable products available commercially, for example of monovalent products, include AronixM-101, M-102, M-111, M-113, M-117, M-152, TO-1210(from Toagosei Co., Ltd.,), KAYARAD TC-110S, R-564, R-128H, (from Nippon Kayaku Co., Ltd.), Biscoat192, Biscoat220, Biscoat2311HP, Biscoat2000, Biscoat2100, Biscoat2150, Biscoat8F, Biscoat17F, (from Osaka Yuki Chemical Ind.,).

And, for example of polyvalent products, include SA1002, (from Mitsubishi Chemical Co., Ltd.,), Biscoat195, Biscoat230, Biscoat260, Biscoat215, Biscoat310, Biscoat214HP, Biscoat295, Biscoat300, Biscoat360, BiscoatGPT, Biscoat400, Biscoat700, Biscoat540, Biscoat3000, Biscoat3700, (from Osaka Yuki Chemical Ind.,), KAYARAD FR-526, HDDA, NPGDA, TPGDA, MANDA, R-551, R-712, R-604, R-684, PET-30, GPO-303, TMPTA, THE-330, DPHA, DPHA-2H, DPHA-2C, DPHA-2I, D-310, D-330, DPCA-20, DPCA-30, DPCA-60, DPCA-120, DN-0075, DN-2475, T-1420, T-2020, T-2040, TPA-320, TPA-330, RP-1040, RP-2040, R-011, R-300, R-205, (from Nippon Kayaku Co., Ltd.), AronixM-210, M-220, M-233, M-240, M-215, M-305, M-309, M-310, M-315, M-325, M-400, M-6200, M-6400, (from Toa Gosei Co., Ltd.), Light Acrylate BP-4EA, BP-4PA, BP-2EA, BP-2PA, DCP-A, (from Kyoeisha Chemical Co., Ltd.), NewfrontierBPE-4, TEICA, BR-42M, GX-8345, (from Dai-Ichi Kogyo Seiyaku Co., Ltd.), ASF-400, (from Nippon Steel Chemical Co., Ltd.) Ripoxy SP-1506, SP-1507, SP-1509, VR-77, SP-4010, SP-4060, (from Showa Highpolymer Co., Ltd.), NK EsterA-BPE-4, (from Shin-Nakamura Chemical Co., Ltd.).

The above radically polymerizing organic substances may be used independently or in combination to attain a desired property.

It is also preferable that 50% by weight or more based on the radically polymerizing organic substance is a compound having (meth)acrylic group in the molecule.

The content of the radically polymerizing organic substance used in the present invention is preferably not more than 200 parts by weight, particularly preferably 10 to 100 parts by weight, based on 100 parts by weight of the cationically polymerizing organic substances.

The (4) energy beam sensitive radical polymerizing initiator, used in the present invention, is a compound, which enables to initiate the radical polymerization upon exposure to an energy beam, and preferably includes ketone series compounds such as acetophenone series compounds, benzyl series compounds and thioxanthone series compounds.

Acetophenone series compounds include, for example, diethoxyacetophenone, 2-hydroxy-2-methyl-1-phenylpropane-1-one, 4'-iso-propyl-2-hydroxy-2-methylpropiophenone, 2-hydroxymethyl-2-methylpropiophenone, 2,2-dimethoxy-1,2-diphenylethane-1-one, p-dimethylaminoacetophenone, p-tert-butyldichloroacetophenone, p-tert-butyltrichloroacetophenone, p-azidobenzalacetophenon, 1-hydroxycyclohexylphenylketone, 2-methyl-1-[4-(methylthio)phenyl]-2-morpholinopropanone-1, 2-benzyl-2-dimethylamino-1-(4-morpholinophenyl)-butanone-1, benzoin, benzoin methyl ether, benzoin ethyl ether, benzoin isopropyl ether, benzoin-n-butyl ether, benzoin isobutyl ether, 1-[4-(2-hydroxyethoxy)-phenyl]-2-hydroxy-2-methyl-1-propane-1-on, and the like.

Benzyl series compounds include benzyl, anisyl and the like.

Benzophenone series compounds include, for example, benzophenone, methyl o-benzoyl benzoate, Michler's ketone, 4,4'-bisdiethylamino benzophenone, 4,4'-dichlorobenzophenone, 4-benzoyl-4'-methyldiphenyl sulfide and the like.

Thioxanthone series compounds include thioxanthone, 2-methylthioxanthone, 2-ethylthioxanthone, 2-chlorothioxanthone, 2-isopropylthioxanthone, 2,4-diethylthioxanthone and the like.

Other energy beam sensitive radical polymerizing initiators include 2,4,6-trimethylbenzoyldiphenyl phosphine oxide, bis(cyclopentadienyl)-bis[2,6-difluoro-3-(pyl-1-yl)] titanium and the like.

The above energy beam sensitive radical polymerizing initiators may be used independently or in combination to attain a desired property.

The content of the (4) energy beam sensitive radical polymerizing initiator described above can be stoichiometric quantity, and it is preferably 0.05 to 10% by weight, more preferably 0.1 to 10% by weight, based on the weight of the (3) radically polymerizing organic substances. When the content exceeds this range, the cured articles have insufficient strength, and in the case of below the cure of the resin is insufficient.

Any component of the photo-polymerizable composition described above is also useful for the (3) radically polymerizing organic substances and the (4) energy beam sensitive radical polymerizing initiator, which are used for the stereolithographic resin composition of the present invention.

The curing rate of the stereolithographic resin composition of the present invention containing the (4) energy beam sensitive radical polymerizing initiator, mixed with the (3) radically polymerizing organic substance described above, exhibits much improved in the stereolithographic process, compared with the other composition, thus such composition is preferable for stereolithographic resin composition.

(5) Organic compounds having two or more hydroxyl groups in a molecule and (6) thermoplastic polymers, may be added in the photo-polymerizable resin composition of the present invention as optional components.

Preferable examples of the (5) organic compounds having two or more hydroxyl groups in a molecule, include polyhydric alcohols, polyethers containing hydroxy groups, polyesters containing hydroxy groups and polyhydric phenols.

Examples of the polyhydric alcohols include ethylene glycol, propylene glycol, neopentyl glycol, trimethylolpropane, glycerol, pentaerythritol, dipentaerythritol, 1,3-butanediol, 1,4-butanediol, 1,6-hexanediol, 1,4-cyclohexane dimethanol, 4, 8-bis (hydroxymethyl)tricyclo[$5,2,1,0^{2.6}$] decane, and the like.

The polyether containing hydroxy groups means a compound obtained by adding one or more alkylene oxide to one or more polyhydric alcohols or one or more polyhydric phenols. Examples of the polyhydric alcohols and polyhydric phenols used therein include ethylene glycol, propylene glycol, neopentyl glycol, trimethylolpropane, glycerol, pentaerythritol, dipentaerythritol, 1,3-butanediol, 1,4-butanediol, 1,6-hexanediol, bisphenol A, bisphenol F, phenol novolac, cresol novolac and the like. On the other hands, examples of the alkylene oxides include propylene oxide, ethylene oxide and the like.

Further, examples of the polyester containing hydroxy groups include a polyester obtained by esterificatioin of one or more polyhydric alcohols and/or polyhydric phenols with one or more monobasic or polybasic acids, and a polyester obtained by esterification of one or more lactones with one or more polyhydric alcohols. Examples of the polyhydric alcohols or polyhydric phenols such as those listed above. Examples of the monobasic acids include formic acid, acetic acid, butyl carbonic acid, benzoic acid and the like. Examples of the polybasic acids include adipic acid, terephthalic acid, trimellitic acid and the like. Examples of the lactones include β-propiolactone, and ε-caprolactone. The polyhydric phenol means a compound containing two or more hydroxy groups, bonded directly to aromatic ring, per one molecule, such as bisphenol A, bisphenol F, phenol novolac resin and cresol novolac resin listed above.

The above-mentioned (5) organic compounds having two or more hydroxyl groups in a molecule may be used independently or in combination to attain a desired property.

The content of the (5) organic compound having two or more hydroxy groups in a molecule is preferably 1 to 50 parts by weight based on the 100 parts by weight of the (1) cationically polymerizing organic substances in the resin composition.

The (6) thermoplastic polymer compound is a polymer compound which is in a liquid or solid state at room temperature and can be uniformly mixed with the resin composition at room temperature.

Typical examples of the (6) thermoplastic polymer compounds include polyester, polyvinyl acetate, polyvinyl chloride, polybutadiene, polycarbonate, polystyrene, polyvinyl ether, polyvinylbutyral, polyacrylate, polymethylmethacrylate, polybutene, and styrene-butadiene block copolymer hydrogenated.

Derivatives of the (6) thermoplastic polymer compounds having functional groups such as a hydroxyl, carboxyl, vinyl or epoxy group may also be used.

The photo-polymerizable composition described above, can be applied, as (5) organic compounds having two or more hydroxyl groups in a molecule, and (6) thermoplastic polymer compounds, which are used in the stereolithographic resin composition of the present invention.

The preferable number-average molecular weight of (6) thermoplastic polymer compound as used in the present invention is 1000 to 500000, more preferably 5000 to 100000. A molecular weight outside this range may be practicable; however, an excessively low molecular weight would fall to attain desired improvement in strength, and excessively high one would increase the viscosity of the resin composition, making it unsuited for optical solid molding.

And, the content of (6) thermoplastic polymer compound, is 5 to 50%, preferably 5 to 30% by weight based on the weight of the total of composition. When the content is less than low limit, no effect is observed. In the case of higher content than higher limit, the composition becomes disadvantageous as a stereolithographic resin composition because the viscosity of the composition becomes too high.

The resin composition according to the present invention with (6) thermoplastic polymer compound further improves the mechanical properties of the cured resin in the stereolithographic process, compared with the same composition without it, and as a result, the resulting composition is preferable stereolithographic resin composition.

If desired, a photosensitizer, which is not essential, may be added in the stereolithographic resin composition as well as the photo-polymerizable composition of the present invention. For example, the combination of the photo-sensitizer such as anthracene derivative or pyrene derivative further improves the cure rate compared with the resin composition without the photo-sensitizer, and as a result, more preferable resin composition can be obtained.

Various resin additives, such as thermosensitive cationic polymerizing initiator, inorganic filler, organic filler, coloring agent such as pigment or dye, leveling agent, defoamer, thickener, flame retardant, antioxidant and stabilizer may be added as desired in the amounts of their normal use, provided that they do not impair the advantage of the present invention. As the thermosensitive cationic polymerizing initiator, for example, aliphatic onium salts described in Japanese Patent Application Laid-open No.SHO 57-49613 and SHO 58-37004, can be mentioned.

Various resin additives, such as thermosensitive cationic polymerizing initiator, inorganic filler, organic filler, coloring agent such as pigment or dye, leveling agent, defoamer, thickener, flame retardant, antioxidant and stabilizer may be added as desired in the amounts of their normal use, provided that they do not impair the advantage of the present invention. However, it is preferable that are limited to 150% by weight or below based on the total amount of the stereolithographic resin composition of the present invention, so as not to amplify the distortion of the obtained molding.

In the present invention, the beam, to which the aforementioned stereolithographic resin composition is exposed, is preferably the ultraviolet laser. The example of the beam include helium-cadmium laser, argon ion laser and neodymium-oscillatory laser with an emission wave length converted to one third by combination with non-linear crystal. Also, the beam, in which the energy of the beam with an emission wave length of 345 to 360 nm is more than 70%, based on the total energy of the beam with an emission wave length of 250 to 400 nm, is more preferable.

In that case the beam with an emission wave length of less than 250 nm, or more than 400 nm, is not useful to cure the aforementioned stereolithographic resin composition, that is not useful to activate the energy beam sensitive cationic polymerizing initiator. However, they may be used, if desired.

Thus, the total energy of the beam with an emission wave length of 250 to 400 nm must be more than the required energy enough to cure the aforementioned stereolithographic resin composition, that is enough to activate the energy beam sensitive cationic polymerizing initiator.

If the energy of the beam with an emission wave length of 345 to 360 nm is not more than 70%, based on the total energy of the beam with an emission wave length of 250 to 400 nm, the beam cannot be absorbed enough to cure, so that the depth to be cured for the resin becomes too deep, and the needless cured portion is made owing to cure the needless portion.

Examples of the beam, in which the energy of the beam with an emission wave length of 345 to 360 nm is more than 70%, based on the total energy of the beam with an emission wave length of 250 to 400 nm include Nd oscillatory solid type laser(e.g. Nd-YVO4 laser, Nd-YAG laser) with an emission wave length converted to one third (355 nm) by combination with non-linear crystal, and the laser beam with an emission wave length of 351 nm rich made by treatment through filter from argon ion laser(333 nm, 351 nm and 364 nm).

The first step to carry out the stereolithographic process according to the present invention is to prepare a stereolithographic resin composition from aforementioned essential constituents for the stereolithographic resin composition, optional constituents if desired and the other materials.

This preparing process may be performed in a known manner by, for example, thoroughly mixing the components by blade turbine agitation, roll kneading, or other method. The preferred compounding ratio of (1) through (4) described above, and the types and contents of the additives to be mixed as necessary may be selected according to the aforementioned stereolithographic resin composition of the present invention. Thus obtained stereolithographic resin composition is generally in a liquid state at room temperature.

In the next step, a given portion of the stereolithographic resin composition is exposed to an energy beam to cure the exposed portion thereof, in order to produce a desired thickness of cured layer; then, the cured layer is overlaid with another layer of the energy beam curing resin composition, which is radio-cured in the same manner to produce a cured layer which continuously overlaps the first above-described cured; and the same process is repeated to finally obtain a three-dimensional solid shape.

Figure 2:
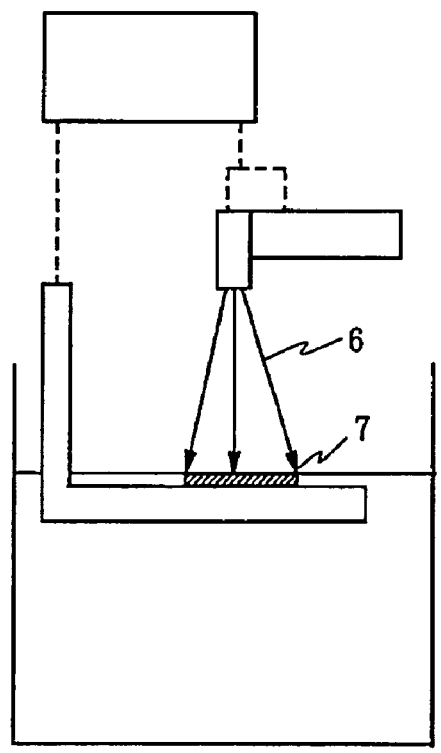
FIG. 2 is an illustration of a step to form a first cured layer in the stereolithographic process.
Figure 3:
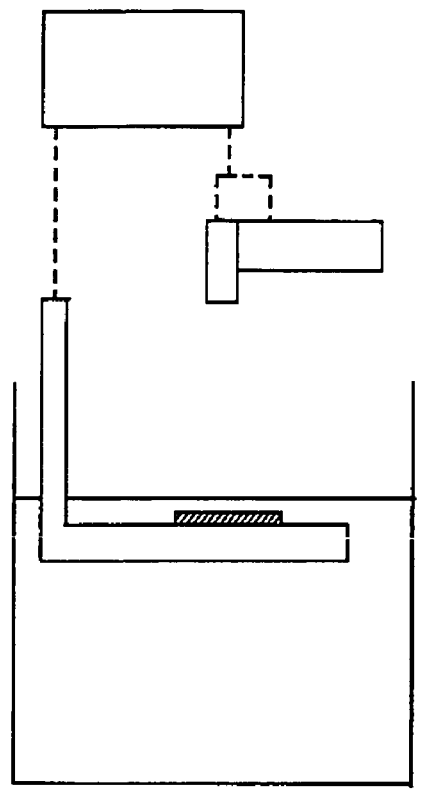
FIG. 3 is an illustration of a step to form a second layer of uncured resin on the first cured layer in the stereolithographic process.
Figure 4:
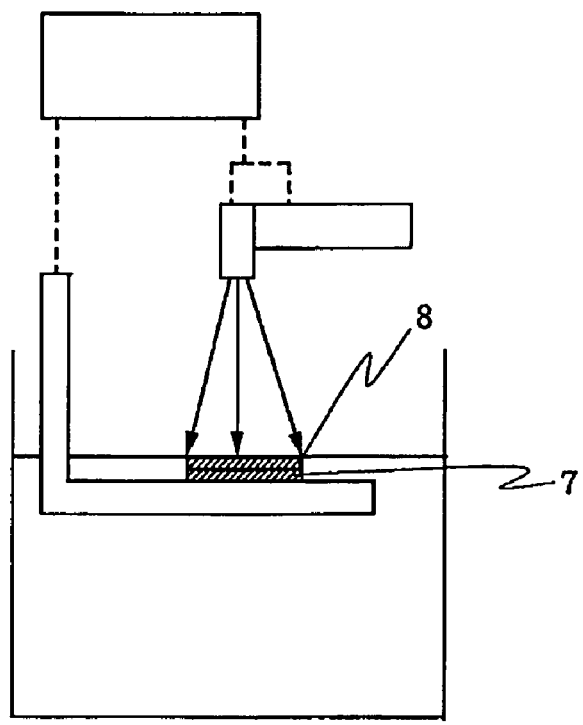
FIG. 4 is an illustration of a step to form a second cured layer in the stereolithographic process.

Furthermore, the process mentioned above is shown according to FIG. 1 through FIG. 4. In FIG. 1 the NC table 2 is set in the resin 5, then the layer of uncured resin is formed with a certain depth, which corresponds to the thickness of the layer of uncured resin. Next, by a signal from control section 1 according to CAD data, the surface of the uncured resin is exposed to scanning radiation by the laser beam 6 from laser source 4 to obtain the first cured layer 7 (cf. FIG. 2). By a signal from control section 1, in turn, the NC table 2 is moved down to form the second layer of uncured resin with the certain thickness on the first cured layer. (cf. FIG. 3). the uncured resin is exposed to scanning radiation by the laser beam 6 in the same manner to obtain the second cured layer 8. (cf. FIG. 4). The same process is repeated to obtain the molding finally.

The following examples are given to illustrate the embodiment of the invention.

SYNTHESIS EXAMPLE-(1)

Synthesis of 2-(8-benzoyl-dibenzothiophenyl)-di-p-tolylsulfonium hexafluoro-antimonate.
(Compound 1.)

82.0 g of benzoyl chloride was added into the mixture of aluminium chloride (93.3 g), dibenzothiophene(107.5 g) and 1,2-dichloroethane(650 g) using 500 mL three necked flask, then reaction was carried out for 2 hrs at 25° C.

The reaction mixture was poured into 1000 g of ice water in a beaker (5000 mL). The 1,2-dichloroethane layer was washed by 1000 g of water three times. After condensing the 1,2-dichloroethane layer under reduced pressure, 160.4 g of 8-benzoyl-dibenzothiophene was obtained (yield 95%).

46.0 g of di-p-tolyl sulfoxide were added into 295 g of 95% sulfuric acid with stirring using 500 mL three necked flask. As soon as adding, the reaction mixture was colored to dark brown. And, 57.6 g of 8-benzoyl-dibenzothiophene obtained above, was added in it. Stirring was continued for 10 hrs at room temperature. Then, the reaction mixture and 300 g of toluene were poured into 500 g of methanol and 500 g of ice in 3000 mL beaker. The underlayer was separated out, and after it was extracted with 500 g of methylene chloride, 1000 g of water was added therein and stirred, and 36.8 g of KSbF$_6$ was added, and stirring was continued for two hours. After the methylene chloride layer was washed with 1000 g of water twice, 90.53 g of a product was obtained as white powder (yield 70%) by condensing under reduced pressure. This product was identified as 2-(8-benzoyl-dibenzothiophenyl)-di-p-tolylsulfonium hexafluoro-antimonate. (Compound 1: the formula shown below)

The results of analysis are shown as follows;

Infrared absorption spectrum(ketone) ν (C=O) 1654 cm$^{-1}$

Identification of chemical structure was carried out by elementary analysis, $^1$H-NMR and $^{13}$C-NMR.

(Compound 1)

SYNTHESIS EXAMPLE-(2)

Synthesis of 2-(8-benzoyl-dibenzothiophenyl)-di-p-tolylsulfonium hexafluoro-phosphate,(Compound 2:the formula shown below)

In the same manner as in Synthesis example (1), KPF$_6$ was used instead of KSbF$_6$. And the Compound 2 was obtained as white powder. Identification was carried out by Infrared absorption spectrum, elementary analysis, $^1$H-NMR and $^{13}$C-NMR.

The result of Elementary analysis is shown as follows:

| Elementary analysis | calcd | found |
|---|---|---|
| C | 61.29% | 61.96% |
| H | 3.90% | 4.18% |
| S | 9.92% | 10.23% |
| P | 4.79% | 4.45% |

(Compound 2).

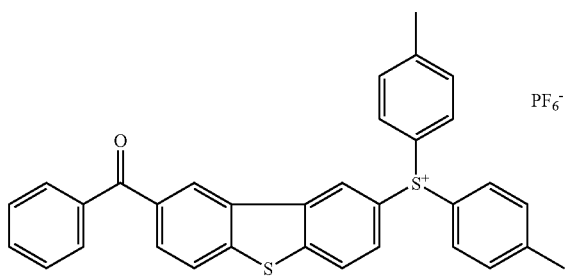

(Compound 2)

SYNTHESIS EXAMPLE-(3)

Synthesis of 2-(8-benzoyl-dibenzothiophenyl)-di-p-fluorophenylsulfonium hexafluoro-antimonate, (Compound 3:the formula shown below)

In the same manner as in Synthesis example (1), di-p-fluorophenyl sulfoxide was used instead of di-p-tolyl sulfoxide. And the Compound 3 was obtained as white powder. Identification was carried out by Infrared absorption spectrum, elementary analysis, $^1$H-NMR and $^{13}$C-NMR.

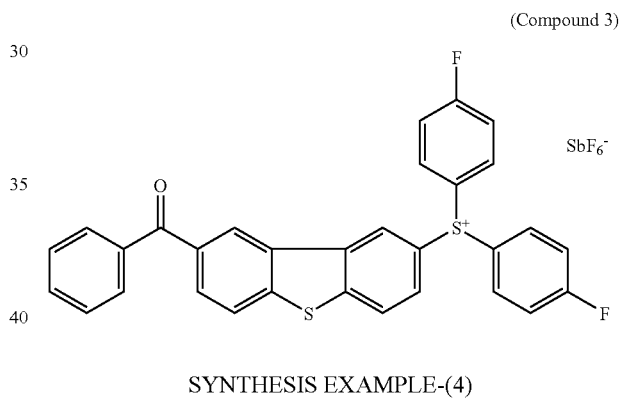

(Compound 3)

SYNTHESIS EXAMPLE-(4)

Synthesis of 2-(8-benzoyl-dibenzothiophenyl)-di-p-fluorophenylsulfonium hexafluoro-phosphate,(Compound 4:the formula shown below)

In the same manner as in Synthesis example (2), di-p-fluorophenyl sulfoxide was used instead of di-p-tolyl sulfoxide. And the Compound 4 was obtained as white powder. Identification was carried out by Infrared absorption spectrum, elementary analysis, $^1$H-NMR and $^{13}$C-NMR.

(Compound 4)

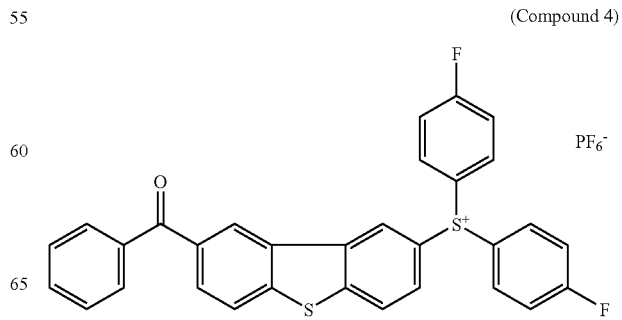

SYNTHESIS EXAMPLE-(5)

Synthesis of
2-(8-benzoyl-dibenzothiophenyl)-diphenylsulfonium
hexafluoro-antimonate,(Compound 5:the formula
shown below)

In the same manner as in Synthesis example (1), diphenyl sulfoxide was used instead of di-p-tolyl sulfoxide And the Compound 5 was obtained as white powder. Identification was carried out by Infrared absorption spectrum, elementary analysis, $^1$H-NMR and $^{13}$C-NMR.

(Compound 5)

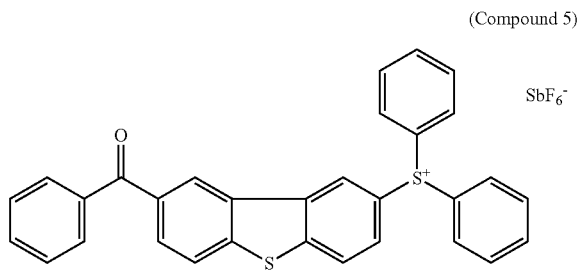

SYNTHESIS EXAMPLE-(6)

Synthesis of
2-(8-benzoyl-dibenzothiophenyl)-diphenylsulfonium
hexafluoro-phosphate,(Compound 6:the formula
shown below)

In the same manner as in Synthesis example (2), diphenyl sulfoxide was used instead of di-p-tolyl sulfoxide. And the Compound 6 was obtained as white powder. Identification was carried out by Infrared absorption spectrum, elementary analysis, $^1$H-NMR and $^{13}$C-NMR.

(Compound 6)

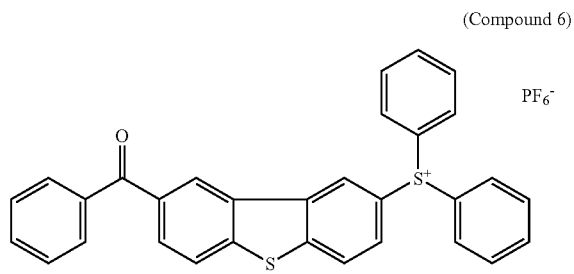

SYNTHESIS EXAMPLE-(7)

Synthesis of 2-(8-benzoyl-dibenzothiophenyl)-di-p-nitrophenylsulfonium hexafluoro-antimonate,(Compound 7:the formula shown below)

In the same manner as in Synthesis example (1), di-p-nitrophenyl sulfoxide was used instead of di-p-tolyl sulfoxide. And the Compound 7 was obtained as white powder. Identification was carried out by Infrared absorption spectrum, elementary analysis, $^1$H-NMR and $^{13}$C-NMR.

(Compound 7)

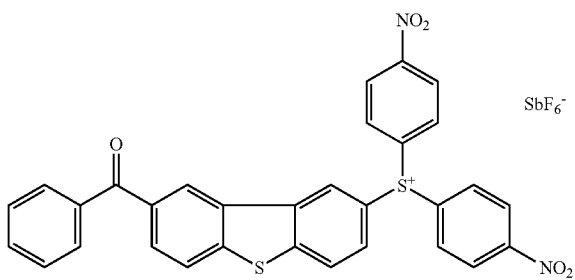

SYNTHESIS EXAMPLE-(8)

Synthesis of 2-(8-benzoyl-dibenzothiophenyl)-di-p-nitrophenylsulfonium hexafluoro-phosphate,(Compound 8:the formula shown below)

In the same manner as in Synthesis example (2), di-p-nitrophenyl sulfoxide was used instead of di-p-tolyl sulfoxide. And the Compound 8 was obtained as white powder. Identification was carried out by Infrared absorption spectrum, elementary analysis, $^1$H-NMR and $^{13}$C-NMR.

(Compound 8)

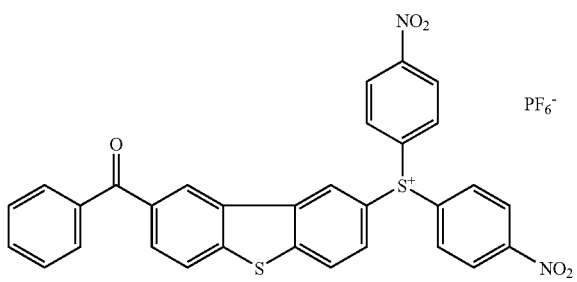

SYNTHESIS EXAMPLE-(8.1)

Synthesis of 2-(8-benzoyl-dibenzothiophenyl)-di-p-benzoylphenylsulfonium hexafluoro-antimonate,
(Compound 8.1:the formula shown below)

In the same manner as in Synthesis example (1), di-p-benzoylphenyl sulfoxide was used instead of di-p-tolyl sulfoxide And the Compound 8.1 was obtained as white powder. Identification was carried out by Infrared absorption spectrum, elementary analysis, $^1$H-NMR and $^{13}$C-NMR.

(Compound 8.1)

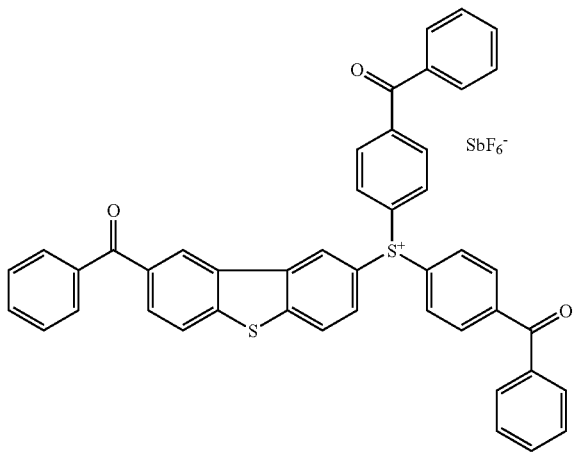

SYNTHESIS EXAMPLE-(8.2)

Synthesis of 2-(8-benzoyl-dibenzothiophenyl)-di-p-benzoylphenylsulfonium hexafluoro-phosphate, (Compound 8.2:the formula shown below)

In the same manner as in Synthesis example (8.1), KPF$_6$ was used instead of KSbF$_6$. And the Compound 8.2 was obtained as white powder. Identification was carried out by Infrared absorption spectrum, elementary analysis, $^1$H-NMR and $^{13}$C-NMR.

(Compound 8.2)

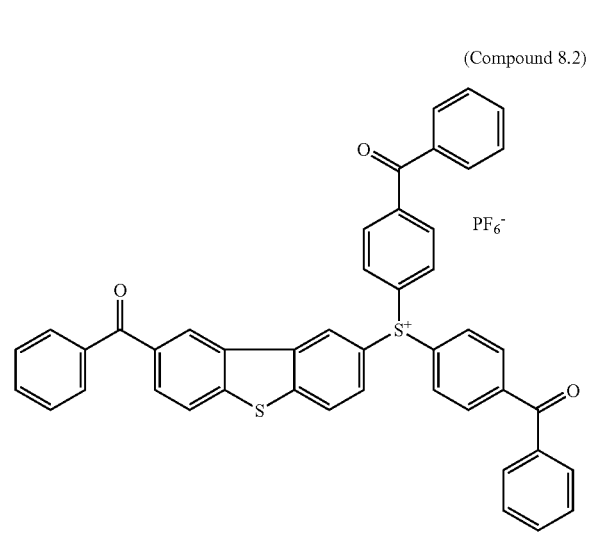

SYNTHESIS EXAMPLE-(8.3)

Synthesis of 2-(8-benzoyl-dibenzothiophenyl)-di-p-acetylphenylsulfonium hexafluoro-phosphate,(Compound 8.3:the formula shown below)

In the same manner as in Synthesis example (2), di-p-acetylphenyl sulfoxide was used instead of di-p-tolyl sulfoxide. And the Compound 8.3 was obtained as white powder. Identification was carried out by Infrared absorption spectrum, elementary analysis, $^1$H-NMR and $^{13}$C-NMR.

(Compound 8.3)

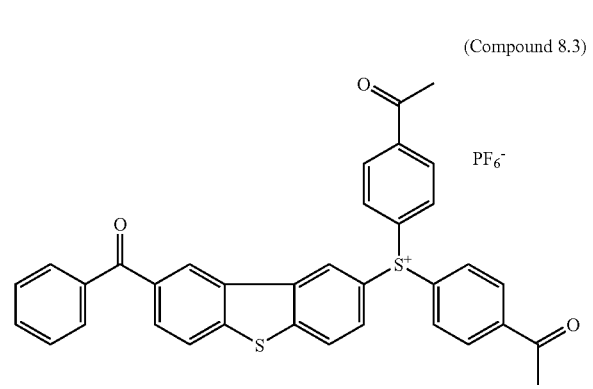

SYNTHESIS EXAMPLE-(8.4)

Synthesis of 2-(8-benzoyl-dibenzothiophenyl)-dibenzothiophenium hexafluoro-phosphate,(Compound 8.4:the formula shown below)

In the same manner as in Synthesis example (2), dibenzothiophenyl sulfoxide was used instead of di-p-tolyl sulfoxide. And the Compound 8.4 was obtained as white powder. Identification was carried out by Infrared absorption spectrum, elementary analysis, $^1$H-NMR and $^{13}$C-NMR.

(Compound 8.4)

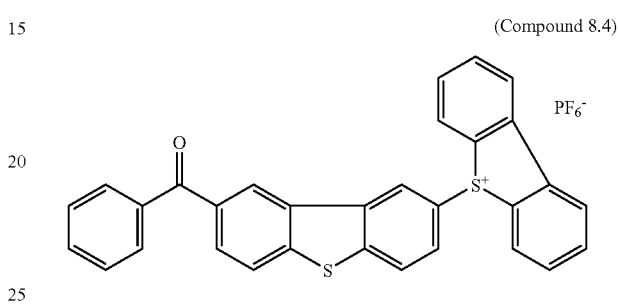

SYNTHESIS EXAMPLE-(8.5)

Synthesis of 2-(8-benzoyl-dibenzothiophenyl)-2-benzoyl-dibenzothiophenium hexafluoro-antimonate, (Compound 8.5:the formula shown below)

In the same manner as in Synthesis example (1), benzoyl-dibenzothiophenyl sulfoxide was used instead of di-p-tolyl sulfoxide And the Compound 8.5 was obtained as white powder. Identification was carried out by Infrared absorption spectrum, elementary analysis, $^1$H-NMR and $^{13}$C-NMR.

(Compound 8.5)

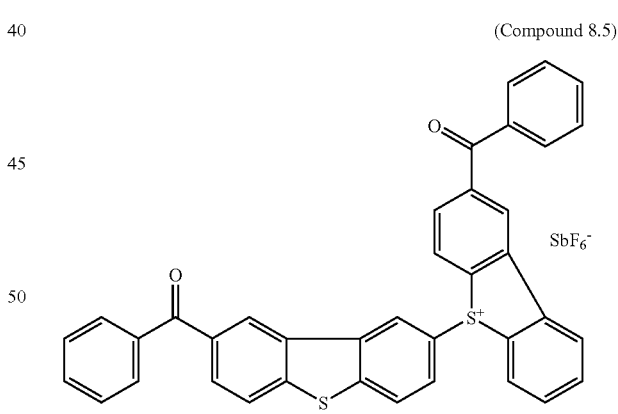

SYNTHESIS EXAMPLE-(8.6)

Synthesis of 2-(8-benzoyl-dibenzothiophenyl)-2-benzoyl-dibenzothiophenium hexafluoro-phosphate, (Compound 8.6:the formula shown below)

In the same manner as in Synthesis example (8.5), KPF$_6$ was used instead of KSbF$_6$. And the Compound 8.6 was obtained as white powder. Identification was carried out by Infrared absorption spectrum, elementary analysis, $^1$H-NMR and $^{13}$C-NMR.

(Compound 8.6)

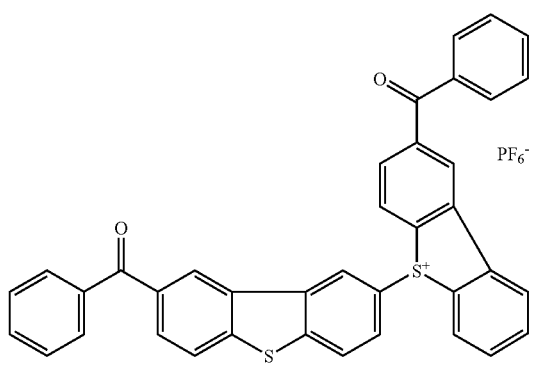

SYNTHESIS EXAMPLE-(8.7)

Synthesis of 2-(8-toluoyl-dibenzothiophenyl)-2-toluoyl-dibenzo-thiophenium hexafluoro-phosphate, (Compound 8.7:the formula shown below)

In the same manner as in Synthesis example (2). 8-toluoyl-dibenzothiophene was used instead of 8-benzoyl-dibenzothiophene, and toluoyl-dibenzothiophenyl sulfoxide was used instead of di-p-tolyl sulfoxide. And the Compound 8.7 was obtained as white powder. Identification was carried out by Infrared absorption spectrum, elementary analysis, $^1$H-NMR and $^{13}$C-NMR.

(Compound 8.7)

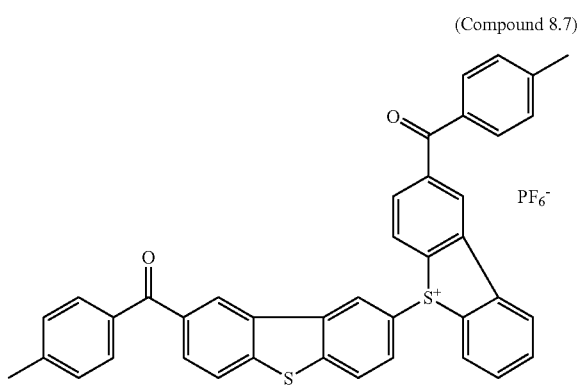

The following compounds were also tested for comparative test.

(Compound 9: the following formula)

-continued (Compound 10: the following formula)

SYNTHESIS EXAMPLE-(11)

Synthesis of 2-dibenzothiophenyl-bis-(2,4,5-trimethylphenyl) sulfonium hexafluorophosphate(Compound 11)

57.3 g(0.2 mol) of bis-(2,4,5-trimethyl) sulfoxide were added into 300 g of 95% (conc.) sulfuric acid with stirring using 1-L three necked flask. After bis-(2,4,5-trimethyl) sulfoxide was dissolved clearly, five aliquots of dibenzothiophene (total 36.7 g (0.2 mol)) were added sequentially.

As soon as adding, the reaction mixture was colored to dark brown. Stirring was continued for 24 hrs at room temperature.

Then, the reaction mixture and 300 g of toluene were poured into 500 g of methanol and 500 g of ice in 3-L beaker. The underlayer was separated out, and after it was neutralized with 40% aqueous sodium hydroxide solution, 1500 g of 1,2-dichloroethane was added therein, and stirring was continued. 66 g of KPF$_6$ was added therein, and stirring was continued for two hours.

After the 1,2-dichloroethane layer was washed with 1000 g of water twice, brown solid was obtained by condensing under reduced pressure. This product was purified by recrystallization with 300 g of ethyl acetate, then 60.0 g of the product was obtained as white powder.

The results of analysis are shown as follows;

| | Elementary analysis | |
| --- | --- | --- |
| | calcd | found |
| C | 60.2% | 60.1% |
| H | 4.9% | 5.0% |
| S | 10.7% | 10.4% |
| P | 5.2% | 5.2% |

($^1$H-NMR, DIMSO-d$_6$)

| peak intensity | chemical shift |
| --- | --- |
| S, 3H—CH$_3$ | 2.50 |
| S, 3H—CH$_3$ | 2.47 |
| S, 3H—CH$_3$ | 2.43 |
| m, 11H-Arom | 6.97~9.05 |

According to the analytical result above, and Infrared absorption spectrum, the chemical structure of the product was identified as follows, (Compound 11)

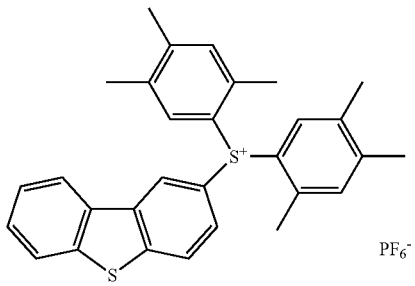

Yield 50%, purity by liquid chromatography was 99.0%.

SYNTHESIS EXAMPLE-(12)

Synthesis of
2-dibenzothiophenyl-bis-(3-methyl-4-butoxyphenyl)
sulfonium hexafluorophosphate(Compound 12)

In the same manner as in Synthesis example (11), 74.8 g(0.2 mol) of bis-(3-methyl-4-butoxy) sulfoxide was used instead of 57.3 g(0.2 mol) of bis-(2,4,5-trimethyl) sulfoxide. And 66.1 g of the product was obtained.

The analytical result of the product was shown as follows.

| | Elementary analysis | |
|---|---|---|
| | calcd | found |
| C | 63.6% | 64.0% |
| H | 4.7% | 4.5% |
| S | 4.9% | 4.9% |
| P | 4.7% | 4.8% |

Owing to the analytical results above, $^1$H-NMR and Infrared absorption spectrum, the chemical structure of the product was identified as follows.

(Compound 12)

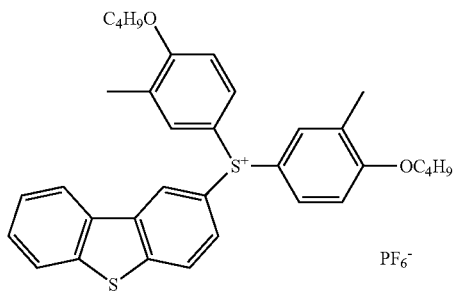

Yield 50%, purity by liquid chromatography was 98.5%.

SYNTHESIS EXAMPLE-(13)

Synthesis of
2-dibenzothiophenyl-bis-(2,4,5-trimethylphenyl)
sulfonium hexafluoroantimonate(Compound 13)

In the same manner as in Synthesis example (11), 98.7 g of KSbF$_6$ was used instead of 66 g of KPF$_6$. And 67.1 g of the product was obtained.

The analytical result of the product was shown as follows.

The Results of Elementary Analysis

| | calcd | found |
|---|---|---|
| C | 55.5% | 54.9% |
| H | 4.7% | 4.6% |
| S | 4.8% | 5.0% |
| Sb | 18.1% | 18.7% |

($^1$H-NMR, DIMSO-d$_6$)

| peak intensity | chemical shift |
|---|---|
| S, 3H—CH$_3$ | 2.50 |
| S, 3H—CH$_3$ | 2.47 |
| S, 3H—CH$_3$ | 2.43 |
| m, 11H-Arom | 6.95~9.10 |

Owing to the analytical results above, and Infrared absorption spectrum, the chemical structure of the product was identified as follows.

(Compound 13)

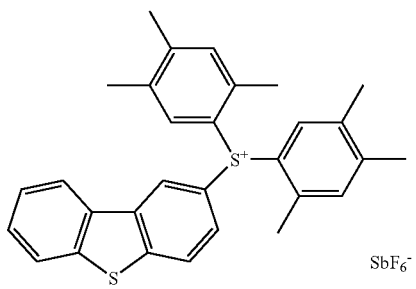

Yield 50%, purity by liquid chromatography was 98.8%.

SYNTHESIS EXAMPLE-(14)

Synthesis of
2-dibenzothiophenyl-bis-(3-methyl-4-butoxyphenyl)
sulfonium hexafluoroantimonate(Compound 14)

In the same manner as in Synthesis example (12), 98.7 g of KSbF$_6$ was used instead of 66 g of KPF$_6$. And 75.9 g of the product was obtained.

The analytical result of the product was shown as follows.

The Results of Elementary Analysis

| | calcd | found |
|---|---|---|
| C | 55.4% | 56.2% |
| H | 5.2% | 5.0% |
| S | 4.2% | 4.3% |
| Sb | 16.0% | 16.3% |

Owing to the analytical results above, $^1$H-NMR and Infrared absorption spectrum, the chemical structure of the product was identified as follows.

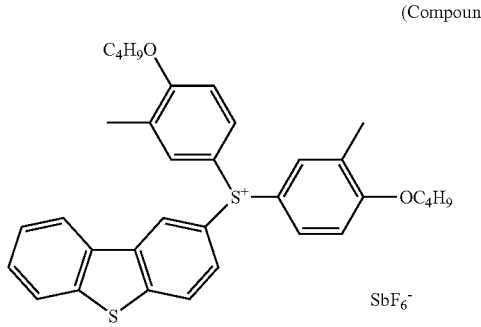

(Compound 14)

Yield 50%, purity by liquid chromatography was 97.5%.

EXAMPLE 1

Spectral Exposure Test

The photo-curable resin composition containing the photo-acid generator, which consists of aromatic sulfonium salt, mentioned above were prepared. The quantity of photo-acid based on 100 g of 3,4-epoxy cyclohexylmethyl-3,4-epoxy cyclohexyl carboxylate are shown in following Table 1. The photo-curable resin composition was coated on a glass plate with bar-coater(No. 6), which was 10 micron thick. The spectral sensitivity of the photo-curable resin composition exposed to an emission wave-length of 365 nm is measured with the use of a spectrometer CT-25CP from Jasco Corporation.

This spectrometer is provided with built-in high-pressure mercury-vapor lamp of 500W and diffraction grating, thus monochromatic light of an emission wave length of 365 nm can be radiated and the radiation energy can be controlled by regulation of the exposing time with the shutter. A movable stage, on which the glass plate coated by the above mentioned photo-polymerizable composition can be set, is provided right below the shutter. The stage can be work in connection with the shutter, and the photo-polymerizable composition can be exposed to thirteen different levels of energy. After exposure, the glass plate, coated with photo-polymerizable composition was developed by methanol. The minimum energy to cure by an emission wave length of 365 nm was determined by the number of the remaining cured film, the luminous energy of an emission wave length of 365 nm and the period of exposure. The test results were shown in Table 1.

TABLE 1

| Compound | Quantity (mmol) | Sensitivity (energy required to cure) (365 nm) (mJ/cm$^2$) |
|---|---|---|
| (1) | 1.0 | 13 |
| (2) | 4.0 | 13 |
| (3) | 1.0 | 13 |
| (4) | 4.0 | 13 |
| (5) | 1.0 | 13 |
| (6) | 4.0 | 13 |
| (7) | 1.0 | 13 |
| (8) | 4.0 | 13 |
| (8.1) | 1.0 | 13 |
| (8.2) | 4.0 | 13 |
| (8.3) | 4.0 | 13 |

TABLE 1-continued

| Compound | Quantity (mmol) | Sensitivity (energy required to cure) (365 nm) (mJ/cm$^2$) |
|---|---|---|
| (8.4) | 4.0 | 13 |
| (8.5) | 1.0 | 13 |
| (8.6) | 4.0 | 13 |
| (8.7) | 4.0 | 13 |
| (9) | 1.0 | 24 |
| (10) | 4.0 | 24 |

In Table 1, it has become clear that the novel sulfonium salts ((1)~(8.7)) of the present invention have more improved sensitivity to long wave radiation with an emission wave length of 365 nm, compared with previously known sulfonium salts (9) and (10).

EXAMPLE 2

Aforementioned compounds (1) to (8.7) were added as photo initiators to the mixture of 80 g of 3,4-epoxy cyclohexylmethyl-3,4-epoxy cyclohexane carboxylate with 20 g of 1,4-butane diol diglycidyl ether at the content as shown in Table 1, and the mixture was blended enough uniformly. The mixture was coated on an aluminium coated paper with bar-coater(No. 3). This sample composition was exposed to radiation from 80 W/cm high-pressure mercury-vapor lamp by the spectrometer provided with belt conveyor. The distance between lamp and belt conveyor was 10 cm and line speed of the belt conveyor was 8 cm/min.

After curing, the sample was held at room temperature for 24 hrs. Then the surface of the sample was tested by return rubbing 200 times with an applicator soaked by MEK (methyl ethyl ketone). As any resin composition was suffered by no damage even after 200 times return rubbing, it was found that the curing was carried out sufficiently and the cured article has good solvent resistance.

EXAMPLE 3

Aforementioned compounds (1) to (8.7) were added as photo initiators to the mixture of 80 g of 3,4-epoxycyclohexylmethyl-3,4-epoxy cyclohexane carboxylate with 20 g of 1,4-butane diol diglycidyl ether at the content as shown in Table 1, and the mixture was blended enough uniformly. The mixture was coated on a polyethylene terephthalate film 50 μm thick with bar-coater(No. 3). This sample composition was exposed to radiation from 80 W/cm high-pressure mercury-vavor lamp by the spectrometer provided with belt conveyor. The distance between lamp and belt conveyor was 10 cm and line speed of the belt conveyor was 8 cm/min.

After curing, the sample was held at room temperature for 24 hrs. Then the pencil hardness of the cured sample was determined by a pencil hardness-tester under 1 kg of load. Every result determined was 2H hardness.

Now, with regard to the stereolithographic resin composition and the stereolithographic process, the examples and the comparative examples are setting forth according to the present invention. In the examples and the comparative examples, the term "parts" means "parts by weight".

Experiment 1: The Precision of the Molding (the Length and the Width) and the Molding Test The stereolithographic resin composition was tested in the stereolithographic experimental system which consisted of a movable NC table, an optical system(together with a laser system) and a control computer, and the box, which is filled with the molding and have the dimension of 100 mm length, 100 mm width and 10 mm height, was obtained from the above resin composition by curing it in steps of 0.1 mm thickness according to CAD data. The differences between the cured article and CAD data about the length and the width, were determined. Also, the properties and the appearance of the model were observed.

Experiment 2: The Determination of the Sensitivity

Using the same system as the Experiment 1, the sensitivity of the resin was tested according to the procedure described in ("Kohsoku sanjigen seikei no kiso" (that is, the basement of the rapid, three dimensional molding), edited and author by Paul F. Jacobs, p. 258, 1993, published by Nikkei Publishing Center).

Experiment 3: The Precision of the Molding (the Thickness of the Needless Cured Portion to the Depth)

Figure 5:
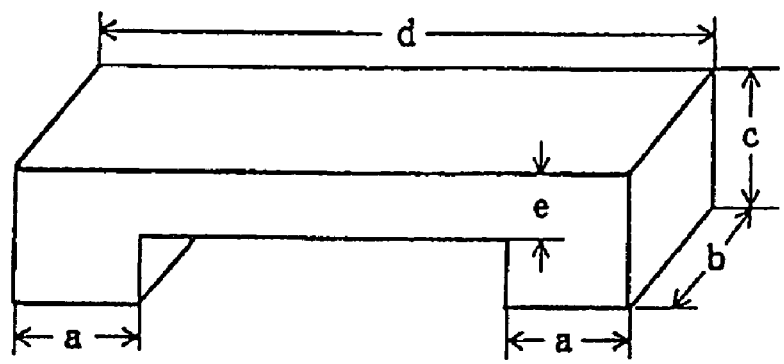
FIG. 5 is an illustration of a specimen used in the Experiment 3 (test for the precision of the molding).

Using the same system as the Experiment 1, except for a specimen used, had a different shape, as shown in FIG. 5 (in the Figure a=b=c=10 mm, d=50 mm, e=5 mm). As shown in the Figure, there is no support under the portion near the center of the specimen. Provided that the absorption of the beam is insufficient, when the resin portion near the center is curing, the needless cured portion is formed. As curing of the needless cured portion is insufficient, this portion is softer compared with the normal cured portion. The thickness of the needless cured portion was determined by being scraped out with a knife.

Experiment 4: The Measurement of the Mechanical Strength

Using the same system as the Experiment 1, a bending test specimen and an impact test specimen were obtained. The specimen were tested for bending strength, Izod impact strength (notched) and elongation in tension according to the test method described in JIS-6911.

The materials used for the Examples and Comparative examples were as follows:

For (1) the cationically polymerizing organic substances hereafter "cationic resins"), cationic resins 1 to 5 as shown below were used:
Cationic resin 1: 3,4-epoxycyclohexylmethyl-3,4-epoxycyclohexane carboxylate.
Cationic resin 2: 1,4-butanedioldlglycidyl ether.
Cationic resin 3: bis(3,4-epoxycyclohexylmethyl) adipate.
Cationic resin 4: bisphenolA diglycidil ether.
Cationic resin 5: 1,4-bis[(3-ethyl-3-oxetanylmethoxy)methyl]benzene For (2) the energy beam sensitive cationic polymerizing initiators (hereafter "cationic initiators"), cationic initiators 1 to 3 as shown below were used:
Cationic initiator 1: Compound 1.
Cationic initiator 2: Compound 3.
Cationic initiator 3: Compound 9.

For (3) the radically polymerizing organic substances (hereafter "radical resins"), radical resins 1 to 3 as shown below were used:
Radical resin 1: dipentaerythritol hexaacrylate.
Radical resin 2: acrylate of bisphenolA epoxide.
Radical resin 3: trimethylolpropane triacrylate.

For (4) the energy beam sensitive radical polymerizing initiators (hereafter "radical initiators"), radical initiators 1 and 2 as shown below were used:
Radical initiator 1: 2-hydroxy-2-methyl-1-phenylpropane-1-on.
Radical initiator 2: 1-[4-(2-hydroxyethoxy)phenyl]-2-hydroxy-2-methyl-1-propane-1-on.

Following three kind of laser were applied in the Experiments. Nd-YVO$_4$: Nd-YVO$_4$ laser having an emission wave length converted to one third by combination with non-linear crystal. Wave length: 355 nm, Pulse-oscillatory laser (from Spectra Physics Co., Trade name: BLIO-355Q).
Ar-1: Ultraviolet-oscillatory argon ion laser. Mixed wave length of 333, 351 and 364 nm (from Coherent, Inc. Trade name: INNOVA325. Rate of energy of an emission wave length of 351 nm is 44%).
Ar-2: Ultraviolet-oscillatory argon ion laser. Mixed wave length of 351 nm(main) and 333 nm(minor) (from Coherent, Inc. Trade name: INNOVA325/0165-148-00. Rate of energy of an emission wave length of 351 nm is 76%).

EXAMPLES 4-11, COMPARATIVE EXAMPLE 1

A resin composition mixed at the content as shown in Table 2, was blended enough to obtain the stereolithographic resin composition. The resin composition was a pale yellow, transparent liquid. Using the resin composition, Experiment 1 to 4 was tested by employing the laser shown in Table 2. The test result was shown in Table 2. In the same manner, Example 5 to 11 and Comparative example 1. The test result was shown in Table 2 to 4.

TABLE 2

|  | Examples | | | | | |
| --- | --- | --- | --- | --- | --- | --- |
|  | 4 | 5 | 6 | 7 | 8 | 9 |
| Cationic resin 1 | 75 | 75 | 55 | 55 | 55 | 35 |
| Cationic resin 2 | 25 | 25 | 15 | 15 | 15 | 20 |
| Cationic resin 3 | — | — | — | — | — | 15 |
| Cationic resin 4 | — | — | — | — | — | 20 |
| Cationic initiator 1 | 2 | — | 2 | 2 | 2 | — |
| Cationic initiator 2 | — | 2 | — | — | — | 2 |
| Cationic initiator 3 | — | — | — | — | — | — |
| Radical resin 1 | — | — | 20 | 20 | 20 | 5 |
| Radical resin 2 | — | — | — | — | — | 5 |
| Radical resin 3 | — | — | 10 | 10 | 10 | — |
| Radical initiator 1 | — | — | 0.5 | 0.5 | 0.5 | — |
| Radical initiator 2 | — | — | — | — | — | 0.5 |
| Type of laser | Ar-1 | Ar-1 | Ar-1 | Ar-2 | Nd—YVO$_4$ | Ar-1 |
| Bending strength (kg/cm$^2$) | 700 | 720 | 810 | 800 | 760 | 790 |
| Izod (kg · cm/cm$^2$) | 6.4 | 6.9 | 6.5 | 6.2 | 6.1 | 6.4 |

TABLE 2-continued

|  | Examples | | | | | |
| --- | --- | --- | --- | --- | --- | --- |
|  | 4 | 5 | 6 | 7 | 8 | 9 |
| Precision of moldings (length and breadth) (mm) | 0.010 | 0.010 | 0.010 | 0.009 | 0.007 | 0.009 |
| Sensitivity (mJ/cm$^2$) | 6.1 | 6.3 | 5.1 | 5.4 | 5.9 | 5.2 |
| Precision of moldings (Needless cured portion) (mm) | 0.12 | 0.11 | 0.13 | 0.10 | 0.11 | 0.12 |

TABLE 3

|  | Examples | |
| --- | --- | --- |
|  | 10 | 11 |
| Cationic resin 1 | — | 40 |
| Cationic resin 5 | 100 | 50 |
| Cationic initiator 1 | 2 | 2 |
| Radical resin 1 | — | 10 |
| Radical initiator 1 | — | 0.5 |
| Type of laser | Nd-YVO$_4$ | Nd-YVO$_4$ |
| Bending strength (kg/cm$^2$) | 700 | 880 |
| Izod (kg·cm/cm$^2$) | 7.1 | 6.8 |
| Precision of moldings (length and breadth) (mm) | 0.008 | 0.006 |
| Sensitivity (mJ/cm$^2$) | 6.1 | 6.0 |
| Precision of moldings (Needless cured portion) (mm) | 0.11 | 0.10 |
| Elongation in tension (%) | 8% | 12% |

TABLE 4

|  | Comparative example 1 |
| --- | --- |
| Cationic resin 1 | 55 |
| Cationic resin 2 | 15 |
| Cationic initiator 3 | 2 |
| Radical resin 1 | 20 |
| Radical resin 3 | 10 |
| Radical initiator 1 | 0.5 |
| Type of laser | Ar-1 |
| Bending strength (kg/cm$^2$) | 720 |
| Izod (kg·cm/cm$^2$) | 6.1 |
| Precision of moldings (length and breadth) (mm) | 0.010 |
| Sensitivity (mJ/cm$^2$) | 8.3 |
| Precision of moldings (Needless cured portion) (mm) | 0.15 |

EXAMPLES 12-15, COMPARATIVE EXAMPLE 2

Photo-polymerization initiator containing the photo-acid generator, consisting the aromatic sulfonium salt compound obtained by Synthesis example 11 to 14, were used to prepare the photo-polymerizable composition as shown in Table 5.

TABLE 5

|  | Examples | | | | Comparative example |
| --- | --- | --- | --- | --- | --- |
|  | 12 | 13 | 14 | 15 | 2 |
| Epoxy resin(a) | 80 | 80 | 80 | 80 | 80 |
| Epoxy resin(b) | 20 | 20 | 20 | 20 | 20 |
| BYK307(c) | 0.5 | 0.5 | 0.5 | 0.5 | 0.5 |
| Compound 11 | 4.0 | — | — | — | — |
| Compound 12 | — | 4.0 | — | — | — |
| Compound 13 | — | — | 4.0 | — | — |
| Compound 14 | — | — | — | 4.0 | — |
| Iodonium salt(d) | — | — | — | — | 4.0 |

(a): 3,4-epoxy cyclohexylmetyl-3,4-epoxy cyclohexane carboxylate.
(b): 1,4-butane diol-diglycidyl ether.
(c): levelling agent from Byk chemie Co.
(d): (4-isobutyl-phenyl)-tolyl-iodonium hexafluorophosphate.

An amount of released benzene (hereafter "benzene content"), curable performance and thermo-stability of the each photo-polymerizable composition were tested as follows. Test results were shown in Table 6.

(Benzene Contents)

Each photo-polymerisable composition was coated on an aluminium plate in the proportion of 15.4 g/m$^2$, and this sample composition was cured by expose to radiation of U.V. light of 400 mJ/cm$^2$ from mercury-vapor lamp. 0.5 g of a cured coating film was put into sealed cell, and released benzene was extracted with 50 ml of ethanol, then benzene content was measured by gas-chromatography. When benzene could not be detected, its data was recorded as ND.

(Curable Performance: MEK Rubbing Test)

Each photo-polymerizable composition was coated on an aluminium coated paper with bar-coater(No. 3). This sample composition was exposed to radiation from 80 W/cm high-pressure mercury-vapor lamp by the spectrometer provided with belt conveyor.

The distance between lamp and belt conveyor was 10 cm and line speed of the belt conveyor was 5 cm/min. After curing, the sample was held at room temperature for 24 hrs. Then the coating film of the sample was tested by return rubbing with an applicator soaked by MEK (methyl ethyl ketone), and return times until the coating film was put off, was determined (one return was counted as one times).

(Thermo-stability)

Each photo-polymerizable composition was set at 40° C. in thermostat chamber and its viscosity (Pa·s) was measured periodically.

TABLE 6

|  | Examples | | | | Comparative example |
|---|---|---|---|---|---|
|  | 12 | 13 | 14 | 15 | 2 |
| Benzene content | ND | ND | ND | ND | ND |
| Curable performance | >200 | >200 | >200 | >200 | 10 |
| Thermo stability Start | 235 | 240 | 233 | 241 | 230 |
| After 1 day | 233 | 245 | 238 | 240 | 280 |
| After 15 days | 240 | 248 | 242 | 246 | 450 |
| After 30 days | 240 | 245 | 251 | 253 | 810 |

EXAMPLE 16

The photo-polymerizable composition obtained by Example 12, was used to prepare the U.V. curable ink having the following formulation. Since the U.V. curable ink do not release benzene, it is useful for foods-packing medium.

Formulation for Ink Composition

| Photo-polymerizable composition: | 100 parts by weight. |
|---|---|
| Phthalocyanine blue: | 20 parts by weight. |
| Methyl ethyl kethone: | 100 parts by weight. |
| Anthracene: | 1 parts by weight. |

EXAMPLES 17-20, COMPARATIVE EXAMPLE 3

Photo-polymerizing initiator containing the photo-acid generator, consisting the aromatic sulfonium salt compound obtained by Synthesis example 11 to 14, were used to prepare the photo-polymerizable composition as shown in Table 7.

TABLE 7

|  | Examples | | | | Comparative example |
|---|---|---|---|---|---|
|  | 17 | 18 | 19 | 20 | 3 |
| Epoxy resin(a) | 80 | 80 | 80 | 80 | 80 |
| Epoxy resin(b) | 20 | 20 | 20 | 20 | 20 |
| BYK307(c) | 0.5 | 0.5 | 0.5 | 0.5 | 0.5 |
| Product(1) | 4.0 | — | — | — | — |
| Product(2) | — | 4.0 | — | — | — |
| Product(3) | — | — | 4.0 | — | — |
| Product(4) | — | — | — | 4.0 | — |
| Iodonium salt(d) | — | — | — | — | 4.0 |
| Radical poly. org. sub. (e) | 20 | 20 | 20 | 20 | 20 |
| Radical initiator(f) | 1.0 | 1.0 | 1.0 | 1.0 | 1.0 |

(e): Bisphenol A diglycidyl ether metacrylate.
(f): Diethoxy acetophenone.

Each photo-polymerizable composition was tested like the example 12. The test result was shown at Table 8.

TABLE 8

|  | Examples | | | | Comparative example |
|---|---|---|---|---|---|
|  | 17 | 18 | 19 | 20 | 3 |
| Benzene content | ND | ND | ND | ND | ND |
| Property after curing | >200 | >200 | >200 | >200 | 50 |

TABLE 8-continued

|  | Examples | | | | Comparative example |
|---|---|---|---|---|---|
|  | 17 | 18 | 19 | 20 | 3 |
| Thermo stability Start | 500 | 504 | 502 | 510 | 501 |
| After 1 day | 514 | 517 | 511 | 520 | 527 |
| After 15 days | 528 | 533 | 528 | 535 | 1393 |
| After 30 days | 553 | 554 | 551 | 553 | 2395 |

EXAMPLE 21

The photo-polymerizable composition obtained by Example 17, was used to prepare the U.V. curable ink having the following formulation. Since the U.V. curable ink do not release benzene, it is useful for foods-packing medium.

Formulation for Ink Composition.

| Photo-polymerizable composition: | 100 parts by weight. |
|---|---|
| Phthalocyanine blue: | 20 parts by weight. |
| Methyl ethyl ketone: | 100 parts by weight. |
| Anthracene: | 1 parts by weight. |

INDUSTRIAL APPLICABILITY

It appears that the aromatic sulfonium salt compound of the present invention can be activated by effective absorption of long-wave radiation, and can act as a suitable photo-acid generator. Therefore, since the photo-polymerizable resin composition, which contains the photo-acid generator, can be cured rapidly to give a good cured article, which has improved properties, a photoresist made of this photo-polymerizable resin composition has good sensitivity and good resolution, and furthermore, since the resin composition is also useful as ink for foods-packing medium, it has wide application. By employing the stereolithographic resin compositions, which comprises the aromatic sulfonium salt compound of the present invention, disadvantages of the prior art can be overcome, this resin composition do not suffer from the hindrance to curing by oxygen, can easily give shaped articles having desired sizes by virtue of the high accuracy thereof in curing, owing to the high sensitivity thereof for radiant energy and can be cured with formation of only a little needless cured portion and without formation of ply separation. Thus, the stereolithographic process employing aforementioned resin composition have been provided.

The invention claimed is:

1. An aromatic sulfonium salt compound expressed by a general formula (I),

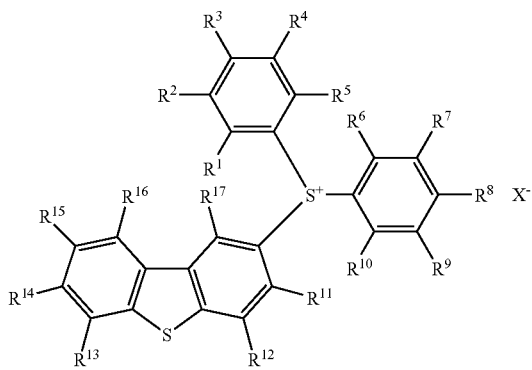

(I)

wherein, $R^1$ to $R^{17}$ are identical or different and are a group selected from the group consisting of hydrogen, halogen, nitro, hydroxyl, alkyl, alkoxy, acyl, phenoxy, ester, aryl, thioether, thiocarbonyl, sulfinyl, sulfonyl, amino, amide, imide, nitrile, phosphino, phospho, phosphoryl and fluoroalkyl groups of 1-8 carbon atoms, wherein the moieties other than the functional groups of these groups can be saturated aliphatic hydrocarbon, unsaturated aliphatic hydrocarbon, alicyclic hydrocarbon, carbocyclic aromatic hydrocarbon or heterocyclic aromatic hydrocarbon of 1-12 carbon atoms, and $R^5$ and $R^6$ can be condensed together with to form a covalent bond, provided that $R^1$ to $R^5$ are not all hydrogen at the same time, and that $R^6$ to $R^{10}$ are not all hydrogen at the same time, X is the same described above, and wherein at least one of $R^1$ to $R^{17}$ is acyl group having of the formula R—CO— or Ar—CO—, where Ar is

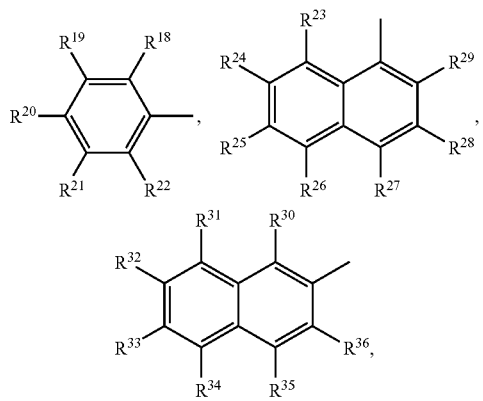

-continued

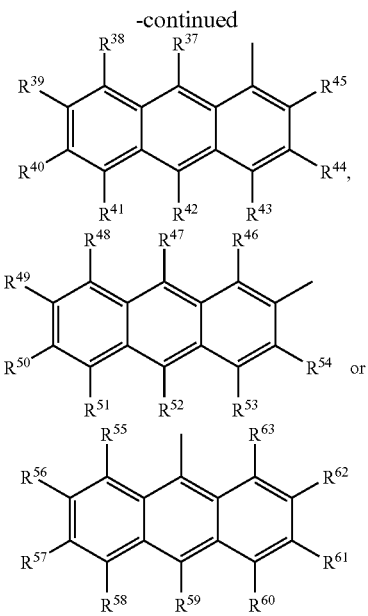

and R is straight or branched alkyl group, or alicyclic hydrocarbon group, and $R^{18}$ to $R^{63}$ are identical or different, respectively hydrogen. halogen, hydroxyl, alkyl or alkoxy.

2. A photo-acid generator comprising an aromatic sulfonium salt compound of claim 1.

3. A photo-polymerizable composition comprising (1) cationically polymerizing organic substances and (2) of claim 2 as an energy beam sensitive cationically polymerizing initiator, as essential components.

4. An ultraviolet curing ink composition which comprises the photo-polymerizable composition of claim 1.

5. An ultraviolet curing ink composition for wrapping material of foods which comprises the photo-polymerizable composition of claim 1.

6. An wrapping material of foods printed by the ultraviolet curing ink composition or the ultraviolet curing ink composition for wrapping material of foods of claim 1.

7. The photo-polymerizable composition of claim 3, which additionally comprises (3) radically polymerizing organic substance and (4) energy beam sensitive radical polymerizing initiator, as essential components.

8. The photo-polymerizable composition of claim 3, wherein at least one among the (1) cationically polymerizing organic substance is an organic compound having one or more epoxy group in a molecule.

9. The photo-polymerizable composition of claim 3, which comprises a compound having a cyclohexenoxide structure in a molecule at the content of 30% by weight or more based on the (1) cationically polymerizing organic substance.

10. The photo-polymerizable composition of claim 7, which comprises a compound having (meth)acrylic group in a molecule at the content of 50% by weight or more based on the (3) radically polymerizing organic substance.

* * * * *

UNITED STATES PATENT AND TRADEMARK OFFICE
CERTIFICATE OF CORRECTION

PATENT NO.      : 7,611,817 B2                                                      Page 1 of 1
APPLICATION NO. : 10/529015
DATED           : November 3, 2009
INVENTOR(S)     : Nakayashiki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1209 days.

Signed and Sealed this

Twelfth Day of October, 2010

David J. Kappos
*Director of the United States Patent and Trademark Office*